US010287573B2

(12) United States Patent
Macula

(10) Patent No.: US 10,287,573 B2
(45) Date of Patent: May 14, 2019

(54) COMBINATORIAL DNA TAGGANTS AND METHODS OF PREPARATION AND USE THEREOF

(71) Applicant: JEANSEE LLC, Geneseo, NY (US)

(72) Inventor: Anthony J. Macula, Geneseo, NY (US)

(73) Assignee: JEANSEE LLC, Geneseo, NY (US)

(*) Notice: Subject to any disclaimer, the term of this patent is extended or adjusted under 35 U.S.C. 154(b) by 1056 days.

(21) Appl. No.: 14/251,690

(22) Filed: Apr. 14, 2014

(65) Prior Publication Data

US 2014/0220576 A1    Aug. 7, 2014

Related U.S. Application Data

(63) Continuation of application No. 12/984,695, filed on Jan. 5, 2011, now Pat. No. 8,735,327.

(60) Provisional application No. 61/292,884, filed on Jan. 7, 2010.

(51) Int. Cl.
| | | |
|---|---|---|
| C12N 15/10 | (2006.01) | |
| C12Q 1/6806 | (2018.01) | |
| C12Q 1/686 | (2018.01) | |
| C12Q 1/6876 | (2018.01) | |

(52) U.S. Cl.
CPC ....... *C12N 15/1065* (2013.01); *C12Q 1/6806* (2013.01); *C12Q 1/686* (2013.01); *C12Q 1/6876* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 5,451,505 | A | 9/1995 | Dollinger |
| 5,674,698 | A | 10/1997 | Zarling |
| 7,112,445 | B1 | 9/2006 | Welle |
| 2007/0172873 | A1 | 7/2007 | Brenner et al. |
| 2008/0261204 | A1 | 10/2008 | Lexow |
| 2010/0105572 | A1 | 4/2010 | Kris et al. |

FOREIGN PATENT DOCUMENTS

WO    2000061799 A2    10/2000

OTHER PUBLICATIONS

Ceulemans et al (1997 Chem. Eur. J. 3:1997-2010).*
Horton et al (BioTechniques 8:528-535) (Year: 1990).*
Fujihashi et al (AIDS Research and Human Retroviruses 11: 461-71) (Year: 1995).*
Brownie et al (Nucleic Acids Research 25:3235-41) (Year: 1997).*
Anthony J. Macula, "Superimposed Code Theoretic Analysis of DNA Codes and DNA Computing," Air Force Research Laboratory Final Technical Report AFRL-RI-RS-TR-2007-288, Jan. 2008. File Name: 20140915_14-251690_IDS_NPL_Cite1.
Anthony J. Macula, Alexander Schliep, Morgan A. Bishop, Thomas E. Renz; "New, Improved, and Practical k-Stem Sequence Similarity Measures for Probe Design," Journal of Computational Biology 15(5): 525-534 (2008). File Name: 20140915_14-251690_IDS-NPL-Cite2.
Hwang, F. K., Liu, Y. C., "Random Pooling Designs Under Various Structures," Journal of Combinatorial Optimization 7, 339-352, 2003. File Name: 20140915_14-251690_IDS_NPL_Cite3.
Gal et al., "Successful preparation and analysis of a 5-site 2-variable DNA library," Natural Computing, vol. 8, Issue 2, 2009. File Name: 20140915_14-251690_IDS_NPL_Cite4.
Arkadii G. D'yachkov, Anthony J. Macula, Wendy K. Pogozelski, Thomas E. Renz, Vyacheslav V. Rykov, David C. Torney; "A Weighted Insertion-Deletion Stacked Pair Thermodynamic Metric for DNA Codes," DNA 2004: 90-103. File Name: 20140915_14-251690_IDS_NPL_Cite5.
Arkadii G. D'yachkov, Anthony J. Macula, Wendy K. Pogozelski, Thomas E. Renz, Vyacheslav V. Rykov, David C. Torney; "New t-Gap Insertion-Deletion-Like Metrics for DNA Hybridization Thermodynamic Modeling," Journal of Computational Biology 13(4): 866-881 (2006). File Name: 20140915_14-251690_IDS_NPL_Cite6.
Morgan A. Bishop, Arkadii G. D'yachkov, Anthony J. Macula, Thomas E. Renz, Vyacheslav V. Rykov; "Free Energy Gap and Statistical Thermodynamic Fidelity of DNA Codes," Journal of Computational Biology 14(8): 1088-1104 (2007). File Name: 20140915_14-251690_IDS_NPL_Cite7.
Anthony J. Macula, Susannah Gal, Cheryl Andam, Morgan A. Bishop, Thomas E. Renz; "PCR Nonadaptive Group Testing of DNA Libraries for Biomolecular Computing and Taggant Applications," Discrete Mathematics, Algorithms and Applications: 1(1) 59-69 (2009). File Name: 20140915_14-251690_IDS_NPL_Cite8.
Marathe et al. "On Combinatorial DNA Word Design," J. Computational Biol.' vol. 8, No. 3; pp. 201-219. EFS File Name: 20140915_14-251690_IDS_NPL_Cite9.
Written Opinion of the International Search authority in PCT application US2012/020326. EFS File Name: 20140915_14-251690_IDS_NPL_Cite10.
Written Opinion of the International Search authority in PCT application US2012/020326. EFS File Name: 20140915_14-251690_IDS_NPL_Cite11.

(Continued)

*Primary Examiner* — Christopher M Gross
(74) *Attorney, Agent, or Firm* — John M. Hammond; Patent Innovations LLC

(57) ABSTRACT

DNA taggants in which the nucleotide sequences are defined according to combinatorial mathematical principles. Methods of defining nucleotide sequences of the combinatorial DNA taggants, and using such taggants for authentication and tracking and tracing an object or process are also disclosed.

5 Claims, 16 Drawing Sheets
Specification includes a Sequence Listing.

(56) References Cited

OTHER PUBLICATIONS

Air Force Research Laboratory Report No. AFRL-RI-RS-TR-2010-19, "Superimposed Code Theoretic Analysis of Deoxyribonucleic Acid (DNA) Codes and DNA Computing," A. Macula, Jan. 2010. EFS File Name: 20140915_14-251690_IDS_NPL_Cite12.
"Molecular beacon: a multitask probe," G. Goel, Journal of Applied Microbiology 2005, 99, 435-442. EFS File Name: 20140915_14-251690_IDS_NPL_Cite13.

* cited by examiner

5' CGTCCATCGT CGCAAGCTGA AGTGGATGCG TCGGTAAGCG TCGGAGTGCT 3'
3' GCAGGTAGCA GCGTTCGACT TCACCTACGC AGCCATTCGC AGCCTCACGA 5'

11000 = CAACCAACCACTCTACCAAC CCTACACCACCTACACCTTT CCTTTCCTCCATCACCTCAT
CCTCACTCTCACTTCCTTCA TCTCCTCTCCACTCAAAACC

00110 = CCAAACCTCCACTTTCCAAC ACACAACTCCTCCACAATCA TCACACACACACACACAATT
CACCTCTCTCACTTCTTCCA TCTCCTCTCCACTCAAAACC

11100 = CAACCAACCACTCTACCAAC CCTACACCACCTACACCTTT TCACACACACACACACAATT
CCTCACTCTCACTTCCTTCA TCTCCTCTCCACTCAAAACC

11110 = CAACCAACCACTCTACCAAC CCTACACCACCTACACCTTT TCACACACACACACACAATT
CACCTCTCTCACTTCTTCCA TCTCCTCTCCACTCAAAACC

US 10,287,573 B2

COMBINATORIAL DNA TAGGANTS AND METHODS OF PREPARATION AND USE THEREOF

CROSS-REFERENCE TO RELATED PATENT APPLICATIONS

This application is a continuation of U.S. non-provisional patent application Ser. No. 12/984,695, which claims priority to U.S. provisional patent Application No. 61/292,884 filed Jan. 7, 2010, the disclosures of which are incorporated herein by reference.

STATEMENT REGARDING FEDERALLY SPONSORED RESEARCH OR DEVELOPMENT

This invention was made with United States Government support. The U.S. Government has a paid-up license in this invention and the right under limited circumstances to require the patent owner to license others on reasonable terms as provided for by the terms of Contract No. FA8750-07-00089 awarded by the United States Air Force, Air Force Material Command, Air Force Research Laboratory/IFKF and National Science Foundation, Small Business Innovation Research (SBIR) Award No. IIP-0944491.

REFERENCE TO A SEQUENCE LISTING

This application is being filed electronically via the USPTO EFS-WEB server, as authorized and set forth in the Manual of Patent Examining Procedure § 1730II.B.2(a)(A), and this electronic filing includes an electronically submitted sequence (SEQ ID) listing. The entire content of this sequence listing is herein incorporated by reference for all purposes. The sequence listing is identified on the electronically filed .txt file as follows:

| FILE NAME | DATE OF CREATION | SIZE |
|---|---|---|
| 20140414_JEA103_SL.txt | Jan. 4, 2011 | 22,314 bytes |

BACKGROUND

Field of the Invention

Taggants utilizing DNA nucleotide sequences, and methods of making, combining and using such taggants.

Description of Related Art

There is an increasing commercial and national need for safe, covert and information-rich marker or "taggant" technology, which can be used in applications such as protecting the public interest, preventing product counterfeiting and piracy, and providing an evidentiary basis to enforce intellectual property rights or defend against unwarranted product liability litigation. There is a need for taggant technology that can generate and detect millions of distinct taggants, and decipher the billions of distinct ways that these taggants can be combined. This need is illustrated in the following broad examples.

The United States Department of Commerce indicates that counterfeiting and piracy cost the U.S. economy between $200 billion and $250 billion per year, are responsible for the loss of 750,000 American jobs, and pose a threat to public health and safety. The FDA alone has seen an 800% increase in the number of new counterfeit drug cases between 2000 and 2006. The Center for Medicine and the Public Interest estimates the sales of counterfeit drugs will reach $75 billion in 2010. The counterfeiting of the drug heparin has been linked to the deaths of between 81 and 149 people in the U.S., and resulted in hundreds of allergic reactions.

Heretofore, a number of patents and publications have disclosed the use of taggant technology, wherein small quantities of certain substances are used as taggants (markers or labels) for tagging, authenticating, tracking, and/or tracing other materials, items, or processes. Among such disclosures are the following, all of which are incorporated herein by reference:

U.S. Pat. No. 5,451,505 to Dollinger discloses methods for tagging and tracing materials using nucleic acids as taggants. In particular, Dollinger discloses a method for tagging a material by treating the material with a nucleic acid taggant so that the nucleic acid attaches to the material in an amount sufficient for subsequent detection. The nucleic acid taggant comprises a specific nucleotide sequence or has a distinct composition of specific nucleotides to facilitate tracing.

International patent application publication WO/2000/061799 of Minton et al. discloses a method of marking a material and subsequently detecting that it has been marked. The method comprises adding or applying a marker comprising a nucleic acid tag to the material, sampling a portion of the material containing the marker, and detecting the presence of nucleic acid tag in the sample. The method is characterized in that the quantity of the nucleic acid tag present in the sample is determined to provide an indication of the quantity of marker present in the material.

U.S. Pat. No. 7,112,445 to Welle discloses a method for identification tagging, and in particular, identification tagging of ammunition. An isotopic taggant is deposited in a layer at the interface between the ammunition primer and propellant so that, as the ammunition is fired, the taggant is dispersed throughout the propellant. The taggant is thus contained in the gunshot residue formed during the firing, and can be read by analysis of residue particles. Reading may be accomplished by employing a binary coding system and a system of authentication tags. The required large number of unique identification tags are obtained by using a fragmented coding system wherein each particle encodes only a portion of an ammunition serial number.

These and other taggant systems notwithstanding, certain problems remain unaddressed in the use of taggants to monitor bulk materials, items, and processes for their manufacture. Depending upon the particular application, a taggant needs to satisfy a broad range of requirements, some of which heretofore have been in conflict with each other. The following is a list of attributes that are desirable in a taggant and/or a set of taggants:

1. Having tens of thousands of unique "signatures" (numerical sequences) in the set of taggants for authenticating, and/or tracking and tracing a large number of targets with a large quantity of aspects (i.e. bits of data).
2. "Deeply layerable," i.e. it should be possible to tag an object with multiple taggants (either simultaneously or over time), wherein the object has undergone a series of manufacturing process steps, and/or is comprised of multiple materials possibly from multiple production batches, and/or is comprised of items that may be from multiple manufacturing plants or suppliers. These are exemplary characteristics; an object may have other characteristics that can be correlated with taggants. The "layered taggants" can be provided on or in the object to represent its various characteristics. The identity of each of the taggant in the layered collection of multiple taggants must be recoverable from the object, and capable of being detected, and analyzed and decoded such that the object can be authenticated, and/or its production history tracked and traced.

3. Nano-scale (i.e. on the order of nanometers dimensionally). This enables taggants to be applied to extremely small structures or items, as well as being covert.
4. Highly covert, i.e. undetectable to an observer, or even undetectable by analysis when it is known or suspected that a taggant is present, but no knowledge of the taggant nature or code is available.
5. Detectable at a parts-per-trillion concentration. This enables low cost use, in that a very small amount of taggant is required to be applied on or in an object to enable subsequent authentication and/or track and trace. Additionally, this attribute facilitates highly covert use.
6. Efficiently decodable, so that the information contained in a taggant, or layered taggants, is easily and quickly accessed.
7. Inert, non-reactive, so that they can be used in a broad range of environments with no interaction with chemicals, heat, light, etc. that are present in an ambient environment.
8. Ingestible, so that they can be used on ingestible products, such as medications.
9. Environmentally safe, so that in use, they do not contaminate an environment or product to which they are applied.
10. Not harmful to internal combustion engines.
11. Useable in solution. By being soluble in a common liquid medium, they can be easily applied in small quantities by simple dispensing equipment.
12. Useable in solids or on solid surfaces, so that they can be easily integrated into an object, or applied to the object.
13. Inexpensive, so that the cost of the taggant is insignificant compared to the cost or value of the product to which it is applied.

In summary, there is both a market need and, in some instances, a legislative imperative for track, trace-back, and authentication technologies. In the field of pharmaceuticals, for example, the Food and Drug Administration Amendments Act (FDAAA) of 2007 directs the FDA to identify and validate effective technologies for the purpose of securing the drug supply chain and for the development of standards for the identification, authentication, and tracking and tracing of prescription drugs.

It is an extremely challenging problem to provide a taggant or set of taggants that has all of the above attributes, or even a large majority of them, in order to satisfy the stringent requirements of complex applications such as pharmaceuticals. To the best of the Applicant's knowledge, there is no taggant currently available which has all of the above listed attributes. There remains a need for such a taggant for providing protection of products and/or processes in fields such as agriculture, banking, defense, environmental protection, homeland security, law enforcement, consumer products, transportation, and public health.

More specifically, as will be explained subsequently herein with regard to the art of DNA taggant technology, small taggant libraries of DNA taggants having relatively short sequences are of limited use in practical applications; and substantially larger desirable taggant libraries having longer sequences needed for bit depth (information content) are extremely difficult to synthesize and are cost-prohibitive. What is needed in this art is a set of DNA taggants that are sufficiently short that they can be provided cost-effectively, while also containing the desired large amount of information in a particular application.

SUMMARY

The present invention meets these needs by providing DNA taggants in which the nucleotide sequences are defined according to principles of combinatorial mathematics. In accordance with the invention, methods of making combinatorial DNA taggants are also provided.

In certain embodiments, a combinatorial DNA taggant in accordance with the invention is provided having a polymerase chain reaction response signal identical to the polymerase chain reaction response signal of an idealized and much longer DNA taggant that is expensive and difficult (or impossible) to synthesize. A method of making a set of such taggants comprises creating a library of idealized DNA taggants from a table of non-cross-hybridizing table-mer sequences, and performing a combinatorial analysis to identify a plurality of combinatorial covering DNA strands to simulate the idealized DNA taggants of the library. The covering strands may then be synthesized, and they may then be combinatorially mixed.

In other embodiments, a combinatorial DNA taggant is provided comprising $n(n-1)/2$ unique bit register encoding strands produced from concatenating n unique DNA table-mers and their reverse complements. A method of making such a taggant comprises defining the set of n single stranded DNA table-mers and their reverse complements, each of the table-mers being different from the other table-mers; and preparing the set of $n(n-1)/2$ unique bit register encoding strands by concatenating the n single stranded DNA table-mers and their reverse complements. Subsets of the $n(n-1)/2$ unique bit register encoding strands may be selected as the combinatorial DNA taggants. Each of the unique combinatorial DNA taggants may be used to represent a unique binary number.

The Applicant's combinatorial method of DNA taggant design and detection enables encoding product, item, or process information as a alpha-numeric sequence represented in DNA in a manner analogous to how a computer stores information in a spreadsheet. This DNA data structure can be read by the laboratory polymerase chain reaction (PCR) method, and then algorithmically decoded to retrieve virtually an unlimited amount of product, item, or process information that has been stored in the instant combinatorial DNA taggants. These taggants can be used to forensically mark objects for anti-counterfeiting, brand protection, liability protection, and other similar security applications.

By virtue of their engineered design, the Applicant's synthetic combinatorial DNA taggants, abbreviated "ComDTags" subsequently herein, are functional at concentrations down to 0.25 parts per trillion. Thus, they cannot be reverse engineered because their detection is only possible with prior knowledge of the taggant-specific DNA sequences required for PCR amplification. The Applicant's DNA taggants differ from all other DNA-based taggants due to the Applicant's combinatorial method, which provides an engineering capability to easily construct millions of unique DNA taggants. In contrast, the current technology known to the Applicant can only obtain on the order of hundreds of uniquely decipherable, and primarily genomic DNA taggants. The easily constructed millions of Applicant's combinatorial DNA taggants are unique, information-rich, and able to be used covertly, providing taggant "signatures," i.e., number patterns and sequences that represent information, that uniquely identify the items and/or processes they label. These signatures can be detected and decoded only by authorized users.

One aspect of the invention is the combination of mathematics and molecular biology to produce the combinatorial DNA taggants. Mathematics is used to design the synthetic DNA that makes the storage of information in ComDTags possible. Then, the specificity of DNA strand recognition and the wet laboratory method of polymerase chain reaction (PCR) is used to generate signals indicative of DNA taggants being present. Finally, mathematics is used to decode the PCR signals and identify the taggant (or layered taggant) signatures and the information they contain.

The information gained by employing ComDTag signatures can be used to prevent counterfeiting and to authenticate, and/or track and trace-back drugs, documents, brand names and manufacturing processes. Moreover, the track and trace-back utility of ComDTag signatures can aid in the prediction, detection and resolution of homeland security threats. Government-issued documents (e.g., passports or currency) may use a ComDTag signature as the unique, forensically covert identifier that matches only one serial number. ComDTags embedded in currency could help to trace money laundering or track the money path of organized crime or terrorist financing. Being stable, non-reactive, covert, and able to be applied on site, ComDTags are well-suited for tagging explosives and their components. Forensics experts investigating terrorist activities could trace such explosives back to a particular store, manufacturing plant and/or geographic location. Being ingestible, ComDTags would be well-suited for tagging drugs and addressing the requirements of the aforementioned FDAAA.

All of the above taggant applications may be enhanced by taggant layering. In certain embodiments, taggant layering may be a combination of an instantaneously detectable overt taggant, and information-rich, highly unique, superimposable and deeply covert taggants such ComDTags. Taggant layering enables a quick initial authentication via the overt taggant, plus a forensic authentication with track and trace-back capability via the instant ComDTags. Accordingly, ComDTags can significantly enhance the utility of existing overt taggants, and thus are especially well-suited to address all of the above exemplary taggant applications. The Applicant's combinatorial DNA taggant system enables decoding of the identity of each ComDTag in a multiple and layered ComDTag signature. This unique ability makes the instant combinatorial DNA taggant system ideal for taggant layering. Through taggant layering decoding, the instant ComDTags can be used to track not only individual components, but they can also be used to trace back and authenticate multi-stage manufacturing processes and supply chains. To the best of the Applicant's knowledge, no other nano-scale and covert taggant system has this capability at any cost.

In general, the decoding of process taggant layering has been an intractable problem for target processes and objects requiring deeply layered taggants. However, with the instant ComDTags being constructed in a combinatorial manner, the decoding of such deeply layered taggants for a process is feasible. Thus, in addition to being covert and information-rich, the instant combinatorial DNA taggants may also be used for both item and process taggant layering.

One exemplary application of the instant ComDTags is their use in tagging other more overt, but instantaneously detectable, taggants. Such overt taggants may be e.g., phosphors, radio frequency identifications (RFIDs), holograms or barcodes. One or more ComDTags and an existing overt taggant may be used together to provide taggant layering of a target. For example, consider the packaging of a pharmaceutical drug. Being theoretically safe for human consumption, covert and nano-size, ComDTags may be used to label the pills in a container, and/or the foil seal for the container. Then the pill container itself (e.g., box, vile) may be taggant layered with both an existing overt tag and a ComDTag. In a subsequent inspection, the overt taggant may be quickly scanned to reveal whether or not the packaging is authentic. Then, to authenticate that the pills in the container are indeed the ones intended to be there, a deeper level of authentication can reveal whether or not the DNA on the pills matches the DNA in the layered taggant on the outside of the box and/or the foil seal. Additionally, the associated ComDTag decoding methods can also discover the absence of a ComDTag, and thereby discover a missing legitimate ingredient or step in the target combination of container and pills.

The pharmaceutical authentication protocol in the above example may be further extended by the deeper layering capabilities of the instant ComDTags. Consider that a manufacturer not only wants a final pill product to be labeled with a taggant, but also wants to ensure that the pill was produced in a legitimate manner with legitimate ingredients and supplies. If a unique ComDTag signature is used to identify each important stage and ingredient, then the final pill is taggant layered with the conglomerate of the ComDTags for the process. This taggant layering can in turn be used to tag the overt taggant. Thus, the instant ComDTags can not only be used to authenticate the pills in the container, they can also simultaneously authenticate the production process thereof. This authentication capability is especially important to a company that want to enhance public safety, while simultaneously protecting itself against unwarranted product defect litigation, since DNA has been established as a highly reliable form of evidence in legal proceedings.

In summary, the Applicant's combinatorial methods provide DNA taggants that are in far greater numbers, are less expensive, carry more item information, are more covert, and are more layerable than all other covert taggants known to the Applicant. Details on the instant combinatorial DNA taggants, methods of providing them, and examples of their use are explained subsequently herein.

BRIEF DESCRIPTION OF THE DRAWINGS

The present disclosure will be provided with reference to the following drawings, in which like numerals refer to like elements, and in which:

FIG. 11 is a listing of the combinatorial DNA taggants (SEQ ID NOS 87-90, respectively, in order of appearance) found to be present in the laboratory demonstration, from an analysis of FIG. 9A and the network graph of FIG. 10;

Figure 1:
FIG. 1 depicts an exemplary double stranded DNA taggant (SEQ ID NO: 11) that can be used to represent an alpha-numeric sequence.

The present invention will be described in connection with certain preferred embodiments. However, it is to be understood that there is no intent to limit the invention to the embodiments described. On the contrary, the intent is to cover all alternatives, modifications, and equivalents as may be included within the spirit and scope of the invention as defined by the appended claims.

DETAILED DESCRIPTION

For a general understanding of the present invention, reference is made to the drawings. In the drawings, like reference numerals have been used where needed to designate identical elements.

As used herein, certain terms are defined as follows:

NUCLEIC ACID: a deoxyribonucleotide or ribonucleotide polymer in either single- or double-stranded form. The nucleotides thereof may include the naturally occurring nucleotide bases adenine, thymine, guanine, cytosine, and uracil, as well as non-naturally occurring nucleotide bases such as those incorporating inosine bases, and derivatized nucleotides, such as 7-deaza-2' deoxyguanosine, methyl- (or longer alkyl) phosphonate oligodeoxynucleotides, phosphorothioate oligodeoxynucleotides, and alpha-anomeric oligodeoxynucleotides.

TAGGANT: In general, a marker placed on, or associated with, an item or process.

DNA TAGGANT: A taggant made of deoxyribonucleic acid having a specific nucleotide sequence or a specific nucleotide composition.

OVERT TAGGANT: A taggant that is detectable by visual inspection, or by a common hand-held instrument such as an ultraviolet lamp, or by a simple procedure such as heating the object containing the taggant.

COVERT TAGGANT: A taggant that is not detectable by visual inspection or by a common hand-held instrument or by a simple procedure; instead, requiring specialized laboratory methods for detection.

TAGGING: The process of treating an item or material with a composition, the taggant, for subsequent identification of the item or material by detection of the taggant.

TRACING: The process of determining the origin or source of an item or material.

TARGET: An item or process to which a taggant has been added or associated.

TAGGANT LAYERING: The association of multiple taggants to a target. The target may be a single item, or a process, or an object comprised of multiple items produced by a process having multiple steps. Taggant layering of a target item may be done by associating multiple taggants to a single item. Taggant layering of a target process or object produced thereby may be done by placing one or more taggants on each item produced in a step in the process. The conglomerate of all taggants in a process is the layered taggant for the process.

Background Information on DNA

As an introduction, the applicant provides the following summary of basic information on DNA, deoxyribonucleic acid. DNA is a nucleic acid that encodes the genetic instructions used in the development and functioning of living organisms. DNA is a long polymer comprising repeating units called nucleotides. It may exist in single stranded form (ssDNA), or double stranded form (dsDNA). In living organisms, DNA is usually present in double stranded form, as a pair of single strand molecules that are held tightly together in an entwined shape commonly referred to as "the double helix."

In a single stranded of DNA, the repeating nucleotide units contain both the segment of the backbone of the molecule, which holds the chain together, and a base. The backbone consists of alternating phosphate and sugar entities. The sugar in DNA is 2-deoxyribose, a pentose (five-carbon) sugar. The sugars are connected by phosphate groups between them, which form phosphodiester bonds between the third and fifth carbon atoms of adjacent sugar rings. These asymmetric bonds provide a reference direction or orientation that can be referred to when describing a single strand of DNA.

The repeating unit of DNA, the nucleotide, consists of a base linked to a sugar and one or more phosphate groups. A series of nucleotides linked together may be referred to as a polynucleotide. In living organisms, these polynucleotide DNA molecules may consist of millions of nucleotide units.

In naturally occurring DNA, any nucleotide in a strand has one of four bases: adenine, thymine, guanine, and cytosine, abbreviated as A, T, G, and C, respectively. A single strand of DNA may be characterized by its nucleotide sequence, with reference to the direction of the strand, i.e., whether the sequence is recited beginning from the 5' end having a terminal phosphate group, or the 3' end having a terminal hydroxyl group. Thus the asymmetric ends of DNA strands are referred to as the 5' (five prime) and the 3' (three prime) ends. Accordingly, the very short DNA strand 5'AACG3' differs from 5'GCAA3', but is identical to 3'GCAA5'.

In doubled stranded DNA, the direction of the nucleotides in one strand is opposite to the direction in the other strand, such that at either end of the double stranded molecule, one strand terminates at the 5' end, and the other strand terminates at the 3' end. Each type of base on one strand forms a bond with just one type of base on the other strand in a phenomenon known as complementary base pairing. The individual base pairs are joined by hydrogen bonding, with A bonding exclusively to T (and vice versa), and C bonding exclusively to G (and vice versa). Accordingly, any given single stranded DNA molecule can most easily form double stranded DNA with its "reverse complement" strand DNA, which has the exact nucleotide sequence such that along the double strand, only A-T pairs and C-G pairs occur. If the nucleotide sequence of a single strand of DNA is known, its reverse complement can easily be determined. To obtain the 3' to 5' reverse complement of a 5' to 3' strand of DNA, one simply substitutes A with T and vice versa, and C with G and vice-versa, reciting the base pairs in the 3' to 5' direction.

For example, the 3' to 5' reverse complement of 5'TCGCA3' is 3'AGCGT5'. A double stranded DNA duplex formed between a single strand and its single strand reverse complement is commonly referred to as a Watson-Crick (WC) duplex. The length of single stranded DNA or a double stranded DNA WC duplex is commonly expressed as the number of bases or base pairs (bp), respectively, in the strand or duplex. The length is often referred to using the shorthand suffix "-mer," being short for "polymer." For example, the strand TCGCA is called a "5-mer;" the length of the WC duplex

```
TCGCA
|||||
AGCGT
``` is 5 base pairs.

From this point forward in this disclosure, unless noted otherwise or explicitly shown, all nucleotide sequences of DNA strands are recited in the 5' to 3' direction.

Method of Representing Numerical Sequences Using DNA Nucleotide Sequences

Any finite alpha-numeric sequence can be encoded as a ssDNA (or dsDNA) taggant; and conversely, any ssDNA or dsDNA taggant may be expressed as a finite alpha-numeric sequence. In the following description, all lower case variables such as e.g., n, q, s, and t are natural numbers, i.e. non-negative integers. As used herein, the term "alpha-numeric sequence" is meant to indicate any sequence of alphabetical letters or other symbols in combination with numbers; or a sequence of alphabetical letters or other symbols exclusively; or a sequence of numbers exclusively. The use of the terms "numerical" or "numeric" herein are intended to also include alphabetical letters or other symbols, unless specifically indicated otherwise.

Consider a fixed set of n·q relatively short single strands of DNA, each having a length of t bases, i.e., a fixed set of "t-mers." They may be arrayed in a table having n columns and q rows. This is referred to herein as "t-DNA n by q table code" and denoted using the notation DNA_TC(n,q,t). Table 1 is a simple example of such a table, expressed accordingly as DNA_TC(5,2,10).

TABLE 1

Exemplary table according to table code DNA_TC(5, 2, 10).

| position 0 (SEQ ID NOS 1 and 6) | position 1 (SEQ ID NOS 2 and 7) | position 2 (SEQ ID NOS 3 and 8) | position 3 (SEQ ID NOS 4 and 9) | position 4 (SEQ ID NOS 5 and 10) |
|---|---|---|---|---|
| 0 CGTCCATCGT | CATTCGCGGA | ACAGTTGCCG | TCGGTAAGCG | GAGCGAACCA |
| 1 GCAGAAGCCA | CGCAAGCTGA | AGTGGATGCG | TGCACGAGAC | TCGGAGTGCT |

The sequences in a given table DNA_TC(n,q,t) are also referred to herein as "table-mers." A single stranded DNA taggant library may be generated from the table-mers. The library is the collection of $q^n$ relatively long nt-mer strands of single stranded DNA having lengths of n×t base pairs, which are concatenated from a given table DNA_TC(n,q,t). A member of a single stranded DNA taggant library is referred to herein as an ssDNA taggant (and as an idealized taggant).

The concatenated table-mers may be used to express any finite alpha-numeric sequence. For example, the table-mers from Table 1 may be used to express a series of 32 binary numbers, i.e., $2^5$, or $q^n$ where q=2 and n=5. The binary numbers thus range from 00000 to 11111. Using a specific example, the binary sequence 01101 is encoded as (SEQ ID NO: 11)
CGTCCATCGT CGCAAGCTGA AGTGGATGCG TCGGTAAGCG
TCGGAGTGCT.

Referring to Table 1, it can be seen that the first ten bases of the fifty base sequence is the ten base sequence of the 0 value of position 0, (0,0); the second ten bases of the fifty base sequence is the ten base sequence of the 1 value of position 1, (1,1); the third ten bases of the fifty base sequence is the ten base sequence of the 1 value of position 2, (2,1); the fourth ten bases of the fifty base sequence is the ten base sequence of the 0 value of position 3, (3,0); and the fifth ten bases of the fifty base sequence is the ten base sequence of the 1 value of position 4, (4,1). In making this representation of the binary sequence, each of the table-mers in DNA_TC(5,2,10) may be identified by an ordered pair of (position, value) as shown above. The first coordinate of the pair corresponds to the position (column) and the second coordinate corresponds to the value (row).

Such encoding is possible because only certain collections of sequences are allowed to be in each position (row), and within each collection, distinct strands are assigned distinct numerical values (e.g., CGTCCATCGT=0 (SEQ ID NO: 1), GCAGAAGCCA=1 (SEQ ID NO: 6) for position 0). The sequences are chosen such that they are sufficiently different to prevent errors in analyzing the coding, as will be explained in further detail subsequently herein.

It is straightforward to see that n·q table-mers can be used to make an n by q table, which in turn can be concatenated to make $q^n$ distinct longer DNA taggants encoding each numeric sequence with n digit positions where each digit can range from 0 to q−1. As a further example, a 3×7 table DNA_TC(7,3,12), wherein q=3, n=7, and t=12 consists of 21 table-mers having lengths of 12 nucleotides, which can be concatenated to produce a taggant library of $3^7$ (2187) distinct single strands of DNA having lengths of 84 nucleotides. This library can also represent the number sequence from 0000000 to 2222222 (the number sequence being in base 3).

For every single stranded DNA taggant there is a corresponding double stranded DNA taggant that is the unique WC duplex that contains the single stranded DNA taggant duplexed with its reverse complement (single) strand. Referring to FIG. 1, it can be seen that a ssDNA taggant can be identified with the unique WC dsDNA taggant that contains it (and its reverse complement). Accordingly, the term DNA taggant used herein also includes WC dsDNA taggants. For a given DNA_TC(n,q,t) table code which is designated by the notation M, the notation TAG(n,q,nt) of M may be used to denote the collection of $q^n$ possible distinct double-stranded n·t base pair taggants that can be formed by concatenation. These doubled stranded n·t base pair taggants are also referred to herein as idealized taggants. In this notation convention, each DNA taggant is identified by its top strand, which is written left-to-right in the 5' to 3' direction as shown in FIG. 1. The exemplary DNA taggant 10 in FIG. 1, which represents the binary sequence 01101 as described previously, is a member of TAG(5,2,50) of Table 1.

Polymerase Chain Reaction Laboratory Method

Polymerase chain reaction (PCR) is a technique widely used in molecular biology, forensic science, environmental science, and many other areas. As is disclosed in Wikipedia at http://en.wikipedia.org/wiki/Polymerase_chain_reaction, "The polymerase chain reaction (PCR) is a scientific technique in molecular biology to amplify a single or a few copies of a piece of DNA across several orders of magnitude, generating thousands to millions of copies of a particular DNA sequence. The method relies on thermal cycling, consisting of cycles of repeated heating and cooling of the reaction for DNA melting and enzymatic replication of the DNA. Primers (short DNA fragments) containing sequences complementary to the target region along with a DNA polymerase (after which the method is named) are key components to enable selective and repeated amplification. As PCR progresses, the DNA generated is itself used as a template for replication, setting in motion a chain reaction in which the DNA template is exponentially amplified.

"Almost all PCR applications employ a heat-stable DNA polymerase, such as Taq polymerase, an enzyme originally isolated from the bacterium *Thermus aquaticus*. This DNA polymerase enzymatically assembles a new DNA strand from DNA building blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample to a defined series of temperature steps. These thermal cycling steps are necessary first to physically separate the two strands in a DNA double helix at a high temperature in a process called DNA melting. At a lower temperature, each strand is then used as the template in DNA synthesis by the DNA polymerase to selectively amplify the target DNA. The selectivity of PCR results from the use of primers that are complementary to the DNA region targeted for amplification under specific thermal cycling conditions.

The polymerase chain reaction technique is further described in *The Polymerase Chain Reaction*, Mullis et al., Birkhäuser, Boston, 1994; and in U.S. Pat. No. 4,683,202 of Mullis, "Process for Amplifying Nucleic Acid Sequences," the disclosure of which is incorporated herein by reference.

The PCR technique may be used in detecting DNA taggants that have been applied on or in a target item for authentication and/or track and trace of the item. Consider a simple example in which one dsDNA (or ssDNA) taggant is selected from a taggant library TAG(n,q,nt) of idealized taggants, and applied to a target, such as a capsule containing medicine. All capsules in a given manufacturing production lot are targets and the single dsDNA taggant is applied to all capsules in that lot. Subsequently, a sample of the medicine is purchased at a retail pharmacy under suspicion that it is counterfeit product.

A capsule of the sample under suspicion is tested using the PCR technique. Material from the capsule is subjected to the reagents used in PCR, which include a pair of primers, each primer being a short strand of DNA that can bind to a complementary section of a relatively long single strand of DNA, at which point the DNA polymerase that is present in the PCR reaction medium functions to add the complementary sequences of nucleotides, thereby completing the formation of the WC duplex of that long single strand of DNA. One of the primers is selected to be complementary to the first of the two single strands of the dsDNA taggant that was applied to the target medicine, and may be selected to join at or near the 3' end of that single strand. The other of the primers is selected to be complementary to the second of the two single strands of the chosen dsDNA taggant, and may be selected to join at or near the 3' end of that single strand.

If the capsule is genuine, i.e. not counterfeit, the chosen DNA taggant will be present in the sample placed in the PCR reaction medium, and amplification of the DNA taggant will occur. In the PCR reaction, the dsDNA taggant separates, and the primers form partial duplexes with their complementary regions on each of the single strands. Nucleotides are then added by the DNA polymerase in the 3' to 5' direction to complete the WC duplexes to their respective 5' ends. If at most only one of the two primers used have complementary regions on the target duplex, then essentially no amplification will be detected. If the capsule is counterfeit, in one instance, there will be no DNA taggant, and no amplification will occur, thus confirming it is counterfeit. In another instance, even if it were known that DNA taggants were being added to the capsule, and the counterfeiters added some random sequences of DNA to the counterfeit product, the odds of their selecting the correct sequences that would amplify with both primers is very small (approximately 1 in a trillion if primers are 20-mers).

The capsule or other targets may include multiple or "layered" taggants. For example, if the capsule contains first and second medications within a capsule wall, the first medication could include a first taggant, the second medication could contain a second taggant, and the soluble capsule wall could contain a third taggant. A sample of the capsule and its contained medications may be subjected to the PCR technique, in which three different pairs of primers may be used to amplify all three of the respective taggants if they are present. If all three taggants are not present, the capsule would be proven counterfeit. If less than all three taggants are present, some improper activity is indicated, which can be investigated.

The chosen DNA taggant or taggants may be present in extremely low concentration on or in the target, as low as 0.25 parts per trillion, while still being detectable by amplification via the PCR technique. After amplification occurs in a sample, the exponentially increased concentration of the DNA taggant may be detected by various known methods. One standard method for detection of amplification known as gel electrophoresis uses an electrical separation and detection of DNA substrands on a size separation gel medium. Other more sensitive and faster (e.g., real-time PCR) methods that automate the entire PCR protocol and can detect amplification are also known. For example, one may use the dye based (e.g., Sybr-Green) or probe based (e.g., TaqMan®) real-time PCR methods from Applied Biosystems of Foster City, Calif., that can be performed on suitable PCR apparatus (e.g., the Stratagene 3000 MX Pro of Agilent Technologies Inc. of Santa Clara, Calif.; or the Smart Cycler® of the Cepheid Corporation of Sunnyvale, Calif.; or the Auto-Lid Dual 384-Well GeneAmp® PCR System of Applied Biosystems. An example of the experimental output from dye based PCR is given in FIG. 9B. It can be seen that for the DNA taggants that are present, i.e. those having positive PCR signals, amplification results in strongly detectable fluorescence in about 15-20PCR cycles. In contrast, the primer pairs that match DNA taggants that are not present produce no (i.e. negative) signal.

The preceding example serves to illustrate how the PCR method may be used in the detection of DNA taggants. For a set of relatively short taggants contained in a small taggant library, this example may be applicable. Table 2 depicts an example of such a taggant library, TAG(5,2,50), created from table-mers of DNA_TC(5,2,10) of Table 1.

However, the short taggants and small taggant library of Table 2 are presented herein only for illustration of certain basic concepts. In practice, the taggant library of Table 2 is of limited use for several reasons. Firstly, the length t of the table-mers that are concatenated to form the taggants are only 10 bases long. In order to have more reliability in the PCR method, it is desirable to have the table-mers be significantly longer, on the order of 20-30 bases. Secondly, the bit depth n of the taggants of Table 2 is only 5 digits. In many applications, it is desirable to have significantly greater bit depth, such as between 10 and 20 digits. Thirdly, the value q of the bits in taggants of Table 2 is binary, i.e. 0 and 1. In many applications, it is desirable to have more than just binary values, i.e. q greater than 2.

It is also noted that except for very small sets of DNA taggants, a given dsDNA taggant cannot unambiguously be identified simply through the use of a PCR primer pair that matches the respective 3' ends of the strands. For example, consider the previously discussed the binary sequence 01101 encoded as CGTCCATCGT CGCAAGCTGA AGTGGATGCG TCGGTAAGCG TCGGAGTGCT (SEQ ID NO: 11). A pair of primers is required to amplify the entire sequence, starting at the 3' end of the above strand and at the 3' end of its reverse complement. The primer required for the 3' end of the above strand is AGCACTCCGA (SEQ ID NO: 12). The primer required for the 3' end of the reverse complement of the above strand is CGTCCATCGT (SEQ ID NO: 13). However, these primers will also amplify any other number values beginning in 0 and ending in 1, i.e., 00001, 01001, 00101, 00011, 01011, 00111, and 01111.

In like manner, different primer pairs would be needed to amplify the sequences 0xxx0, 1xxx0, and 1xxx1, where x may be 0 or 1. Each of these represents eight separate numbers. It will be apparent that a strategy of attempting to identify DNA taggants by only initiating amplification at the ends of the strands will be insufficient, unless only four unique taggants are used, because this strategy provides no information on the inner portions of the taggants. Multiple PCR reactions must be run to obtain this information; how to accomplish this in a systematic and cost effective manner that simultaneously allows for layered taggant decoding is a problem which, to the best of the Applicant's knowledge, has not been solved.

TABLE 2

Taggant library TAG(5, 2, 50) created from table-mers of DNA_TC(5, 2, 10) of Table 1.

| numeric sequence | SEQ ID NO: | position 0 | position 1 | position 2 | position 3 | position 4 |
|---|---|---|---|---|---|---|
| 00000 | 14 | CGTCCATCGT | CATTCGCGGA | ACAGTTGCCG | TCGGTAAGCG | GAGCGAACCA |
| 10000 | 15 | GCAGAAGCCA | CATTCGCGGA | ACAGTTGCCG | TCGGTAAGCG | GAGCGAACCA |
| 01000 | 16 | CGTCCATCGT | CGCAAGCTGA | ACAGTTGCCG | TCGGTAAGCG | GAGCGAACCA |
| 11000 | 17 | GCAGAAGCCA | CGCAAGCTGA | ACAGTTGCCG | TCGGTAAGCG | GAGCGAACCA |
| 00100 | 18 | CGTCCATCGT | CATTCGCGGA | AGTGGATGCG | TCGGTAAGCG | GAGCGAACCA |
| 10100 | 19 | GCAGAAGCCA | CATTCGCGGA | AGTGGATGCG | TCGGTAAGCG | GAGCGAACCA |
| 01100 | 20 | CGTCCATCGT | CGCAAGCTGA | AGTGGATGCG | TCGGTAAGCG | GAGCGAACCA |
| 11100 | 21 | GCAGAAGCCA | CGCAAGCTGA | AGTGGATGCG | TCGGTAAGCG | GAGCGAACCA |
| 00010 | 22 | CGTCCATCGT | CATTCGCGGA | ACAGTTGCCG | TGCACGAGAC | GAGCGAACCA |
| 10010 | 23 | GCAGAAGCCA | CATTCGCGGA | ACAGTTGCCG | TGCACGAGAC | GAGCGAACCA |

TABLE 2-continued

Taggant library TAG(5, 2, 50) created from table-mers of DNA_TC(5, 2, 10) of Table 1.

| numeric sequence | SEQ ID NO: | position 0 | position 1 | position 2 | position 3 | position 4 |
|---|---|---|---|---|---|---|
| 01010 | 24 | CGTCCATCGT | CGCAAGCTGA | ACAGTTGCCG | TGCACGAGAC | GAGCGAACCA |
| 11010 | 25 | GCAGAAGCCA | CGCAAGCTGA | ACAGTTGCCG | TGCACGAGAC | GAGCGAACCA |
| 00110 | 26 | CGTCCATCGT | CATTCGCGGA | AGTGGATGCG | TGCACGAGAC | GAGCGAACCA |
| 10110 | 27 | GCAGAAGCCA | CATTCGCGGA | AGTGGATGCG | TGCACGAGAC | GAGCGAACCA |
| 01110 | 28 | CGTCCATCGT | CGCAAGCTGA | AGTGGATGCG | TGCACGAGAC | GAGCGAACCA |
| 11110 | 29 | GCAGAAGCCA | CGCAAGCTGA | AGTGGATGCG | TGCACGAGAC | GAGCGAACCA |
| 00001 | 30 | CGTCCATCGT | CATTCGCGGA | ACAGTTGCCG | TCGGTAAGCG | TCGGAGTGCT |
| 10001 | 31 | GCAGAAGCCA | CATTCGCGGA | ACAGTTGCCG | TCGGTAAGCG | TCGGAGTGCT |
| 01001 | 32 | CGTCCATCGT | CGCAAGCTGA | ACAGTTGCCG | TCGGTAAGCG | TCGGAGTGCT |
| 11001 | 33 | GCAGAAGCCA | CGCAAGCTGA | ACAGTTGCCG | TCGGTAAGCG | TCGGAGTGCT |
| 00101 | 34 | CGTCCATCGT | CATTCGCGGA | AGTGGATGCG | TCGGTAAGCG | TCGGAGTGCT |
| 10101 | 35 | GCAGAAGCCA | CATTCGCGGA | AGTGGATGCG | TCGGTAAGCG | TCGGAGTGCT |
| 01101 | 11 | CGTCCATCGT | CGCAAGCTGA | AGTGGATGCG | TCGGTAAGCG | TCGGAGTGCT |
| 11101 | 36 | GCAGAAGCCA | CGCAAGCTGA | AGTGGATGCG | TCGGTAAGCG | TCGGAGTGCT |
| 00011 | 37 | CGTCCATCGT | CATTCGCGGA | ACAGTTGCCG | TGCACGAGAC | TCGGAGTGCT |
| 10011 | 38 | GCAGAAGCCA | CATTCGCGGA | ACAGTTGCCG | TGCACGAGAC | TCGGAGTGCT |
| 01011 | 39 | CGTCCATCGT | CGCAAGCTGA | ACAGTTGCCG | TGCACGAGAC | TCGGAGTGCT |
| 11011 | 40 | GCAGAAGCCA | CGCAAGCTGA | ACAGTTGCCG | TGCACGAGAC | TCGGAGTGCT |
| 00111 | 41 | CGTCCATCGT | CATTCGCGGA | AGTGGATGCG | TGCACGAGAC | TCGGAGTGCT |
| 10111 | 42 | GCAGAAGCCA | CATTCGCGGA | AGTGGATGCG | TGCACGAGAC | TCGGAGTGCT |
| 01111 | 43 | CGTCCATCGT | CGCAAGCTGA | AGTGGATGCG | TGCACGAGAC | TCGGAGTGCT |
| 11111 | 44 | GCAGAAGCCA | CGCAAGCTGA | AGTGGATGCG | TGCACGAGAC | TCGGAGTGCT |

Now consider an example of a larger taggant library which is made up of table-mers having a sufficient number of nucleotides to ensure reliable PCR results, a larger bit depth, and a larger choice of values in the bits. Such an exemplary taggant library could be created as described previously herein from a 3×10 table, DNA_TC(7,3,20), wherein q=3, n=7, and t=20. Such a table (not shown) consists of 21 table-mers having lengths of 20 nucleotides, which can be concatenated to produce a taggant library of $3^7$ (2187) distinct single strands of DNA having lengths of 140 nucleotides. This library may represent the 2187 number sequence from 0000000 to 2222222. (For use as taggants, the 2187 ssDNA strands would be converted to dsDNA WC duplexes so that the PCR technique could be used in taggant detection.)

A taggant library of this size is needed for many applications; for other applications, the size of the taggant library may be even greater. Nonetheless, there are severe problems in producing a taggant library of this size, with the taggants having such long nucleotide sequences. Firstly, there is an error rate in synthesizing any DNA sequence. The longer the sequence is, the greater the cumulative errors in the nucleotide sequence become, to the point where the nucleotide sequence is not sufficiently accurate to enable the DNA strand to reliably serve as a taggant. Secondly, there is a yield loss rate per nucleotide added, such that the longer the sequence, the disproportionately greater the cost. Thirdly, the overall cost of synthesizing a library of over two thousand taggants would likely be prohibitive for the vast majority of applications. Fourthly, the logistics of precisely managing a library of over two thousand taggants in the environment of their use would be daunting and likely subject to an unacceptable error rate.

In summary, small taggant libraries of taggants having relatively short sequences are of limited use in practical applications, and substantially larger desirable taggant libraries having longer sequences needed for bit depth (information content) are extremely difficult to synthesize and are cost-prohibitive.

What is needed are:

i. A relatively small number of sufficiently short DNA taggants that can be provided cost-effectively.

ii. Methods of combining subsets of these sufficiently short DNA taggants to convey the desired large amount of information for a particular application.

iii. Methods of designing sufficiently short DNA taggants that can be mixed together to avoid PCR errors.

iv. Methods of analyzing the resulting data so that the information contained in a large number of DNA taggants can be decoded and understood with certainty.

DNA Taggants Defined Using Principles of Combinatorial Mathematics

In accordance with the invention, the problem of providing DNA taggants that are sufficiently short to be low in cost, while still individually encoding large amounts of information and collectively forming a sufficiently large library of taggant choices is solved by providing DNA taggants in which the nucleotide sequences are defined according to principles of combinatorial mathematics.

The PCR technique previously described herein may be used advantageously in the methods of the present invention. In certain embodiments, by incubating a DNA taggant mixture with oligonucleotide recognition site PCR primers and the enzyme DNA polymerase, the presence of a pair of recognition sites on a common substrand of a DNA taggant can be determined by whether or not a PCR amplification occurs. This PCR amplification information can be mathematically exploited to detect individual taggants and to detect and decode layered taggants.

In one aspect of the invention, by using smaller DNA fragments that mathematically constitute what is known as a combinatorial cover (hence the name ComDTag), the Applicant's method of defining a set of combinatorial DNA taggants and related method of using such taggants can provide the same information that would be obtained from using a single longer DNA taggant that is prepared in accordance with prior art methods.

Figure 2:
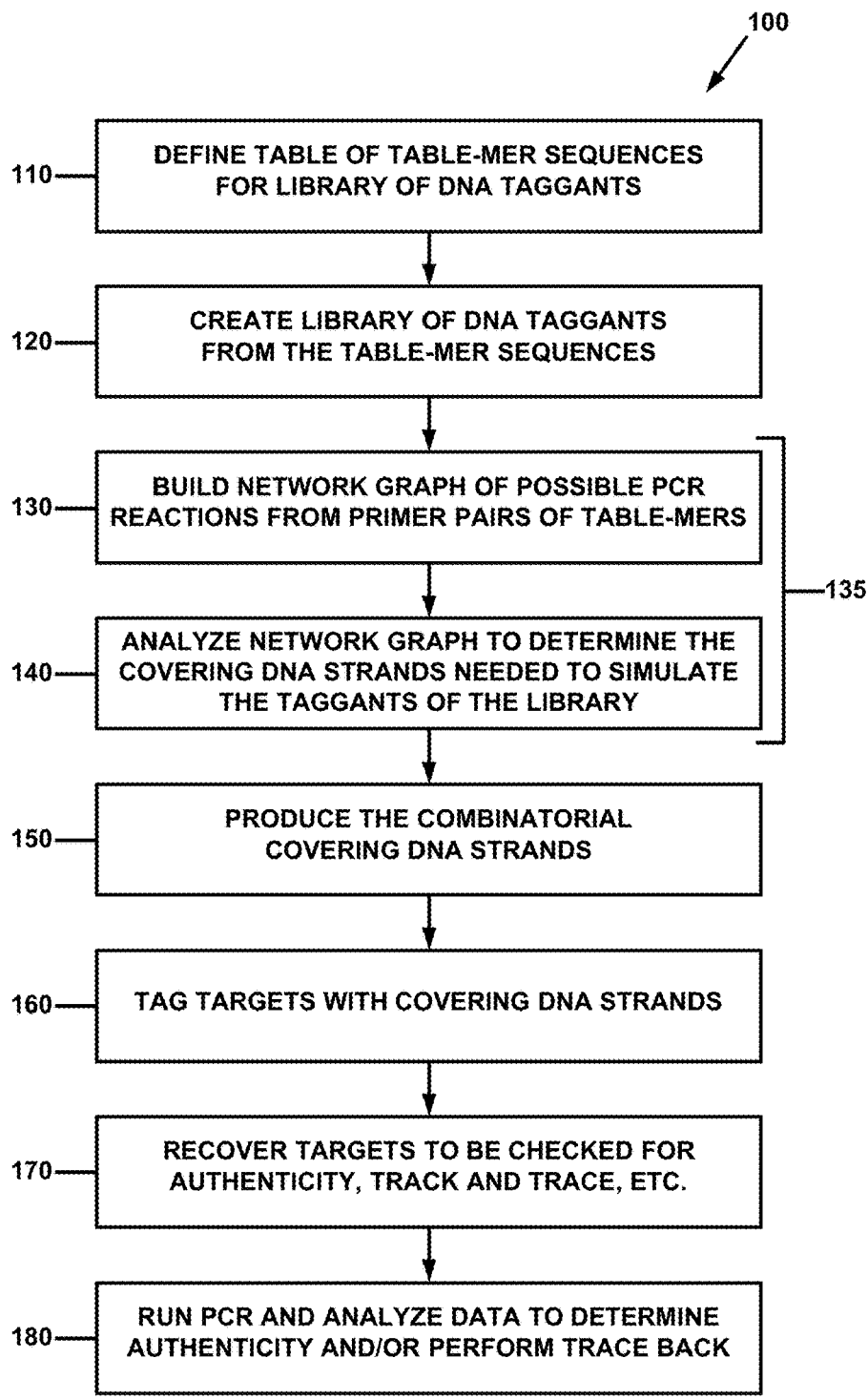
FIG. 2 is a flowchart depicting one embodiment of the Applicant's method of defining a set of combinatorial DNA taggants, and using such taggants in determining authenticity and/or performing trace back of a target object or process.

FIG. 2 is a flowchart depicting one embodiment of the Applicant's method of defining a set of combinatorial DNA taggants and using such taggants. The method 100 comprises defining 110 a table of table-mer nucleotide sequences that can be used to construct a library of DNA taggants, creating 120 the library of taggants, and performing a combinatorial analysis 135 of the table-mer sequences to determine the covering DNA strands needed to simulate the taggants of the library. The combinatorial analysis 135 may be performed by building 130 a network graph of possible PCR reactions from primer pairs of table-mers, and analyzing 140 the network graph to determine the DNA covering strands. It will be seen that the covering DNA strands are much shorter than the DNA taggants of the taggant library, and the number of covering strands needed to simulate all of the DNA taggants of the taggant library is much less than the number of taggants in the library. Thus the instant combinatorial DNA taggants are sufficiently short to be low in cost, while still being capable of encoding large amounts of information and collectively forming a sufficiently large library of taggant choices.

The method 100 will now be explained using the table-mers of the table code DNA_TC(5,2,10) of Table 1, and the associated taggant library TAG(5,2,50) of Table 2. As recited previously, this taggant library is likely to be unsuitable for practical uses; however, because of its simplicity, it is used here for illustrative purposes. Examples of a larger taggant library and its combinatorial cover will be presented subsequently.

It is first noted that for a general taggant library TAG(n, q,nt), there are $n(n-1)q^2/2$ primer pairs of table-mers. Therefore, there are the same number of distinct PCR reactions, with each taggant being positive for exactly $n(n-1)/2$ of them. Accordingly, for the table-mers of Table 1 and all 32 distinct taggants in TAG(5,2,50) formed therefrom and shown in Table 2, n=5 and q=2, so there are 40 distinct PCR reactions which can be performed. Additionally, any given taggant is positive for ten of the PCR reactions.

Figure 3A:
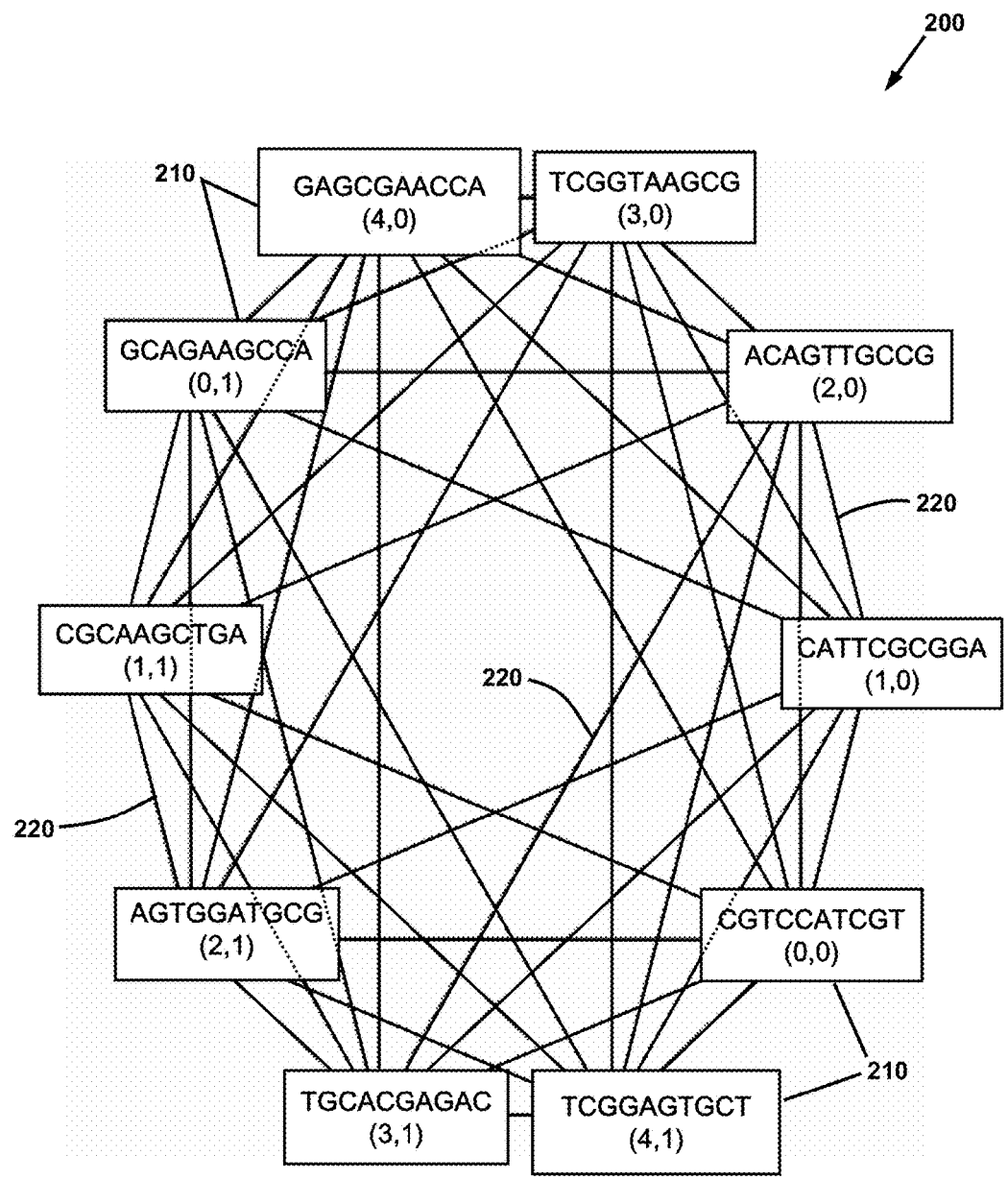
FIG. 3A is an example of a network graph that may be used to define a set of combinatorial DNA taggants and a set of PCR reactions to read the combinatorial DNA taggants according to the method depicted in FIG. 2 (FIG. 3A discloses SEQ ID NOS 1-10, respectively, starting counter-clockwise from the sequence labeled as "(0,0)")

FIG. 3A depicts a network graph 200 that may be used in defining the DNA covering strands for the taggant library of Table 2. In the network graph 200, the ten table-mers 210 of Table 1 are arrayed as a set of nodes in a roughly circular manner. The lines 220 connecting the nodes 210 in the graph 200 denote all possible primer pairs of these table-mers. It is noted that there are no lines between primer pairs with the same first coordinate (such as e.g., (4,0) and (4,1)). This is because no single taggant can have two distinct table-mers at the same position. There are 40 lines 220 (also known as edges in network graph analysis) in FIG. 3A, which show the 40 distinct PCR reactions which can be performed.

Figure 3B:
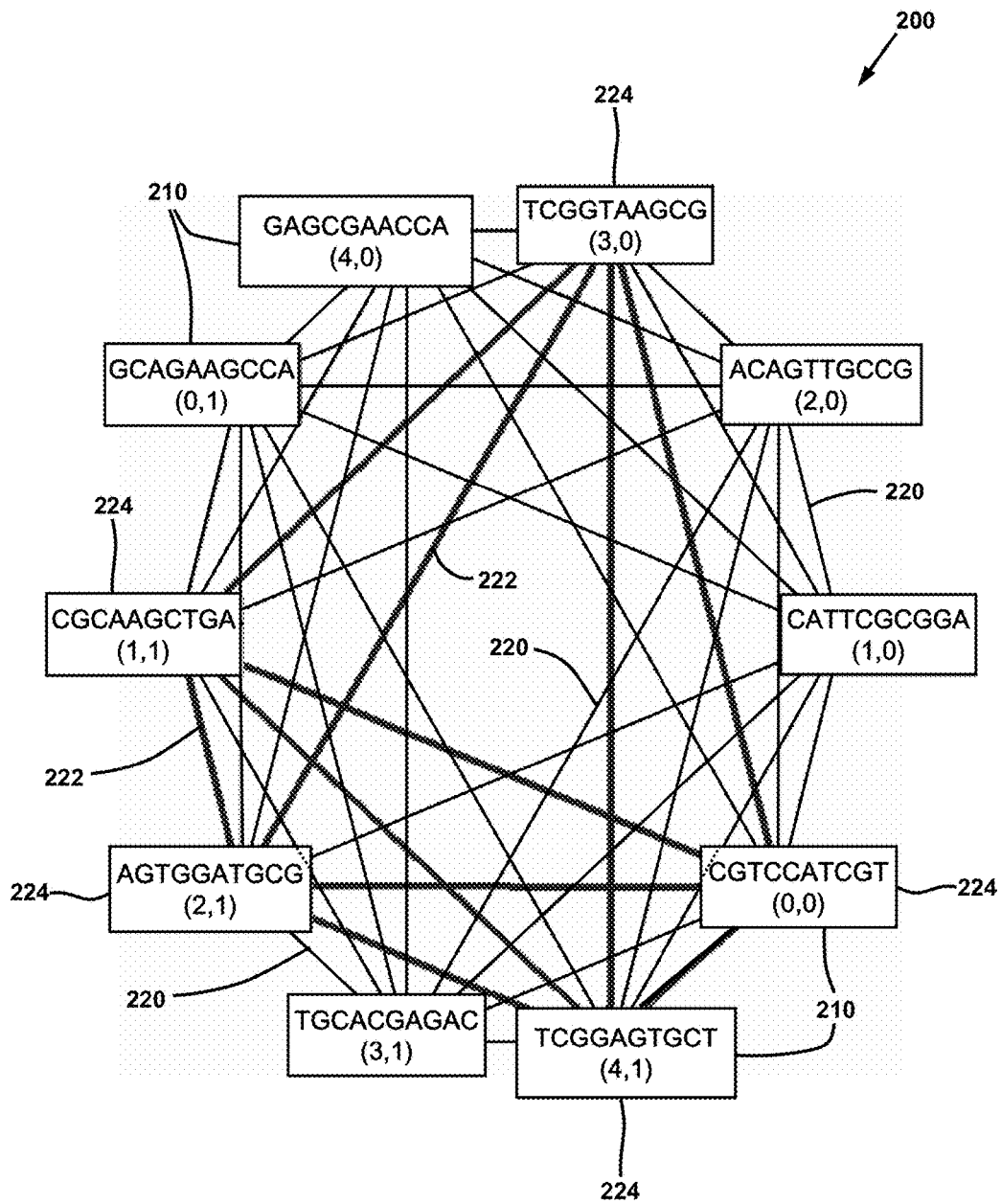
FIG. 3B depicts the network graph of FIG. 3A, modified to identify the set of positive PCR reactions for a specific and idealized DNA taggant represented by a particular alpha-numeric value (FIG. 3B discloses SEQ ID NOS 1-10, respectively, starting counter-clockwise from the sequence labeled as "(0,0)")

FIG. 3B depicts the network graph of FIG. 3A, modified to identify the set of positive PCR reactions for the DNA taggant of Table 2 that is represented by the value 01101. The set of bold lines 222 denotes the set of positive PCR reactions for the DNA taggant represented by 01101. As noted previously, the taggant represented by the numerical value 01101 (SEQ ID NO: 11) is

```
CGTCCATCGT CGCAAGCTGA AGTGGATGCG TCGGTAAGCG
   (0, 0)     (1, 1)     (2, 1)     (3, 0)

TCGGAGTGCT.
   (4, 1)
```

For clarity in correlating the above with FIG. 3B, the respective ordered pairs of the individual digits are also shown. It can be seen in FIG. 3B that bold lines are shown between the following table-mers: (0,0)↔(1,1); (0,0)↔(2,1); (0,0)↔(3,0); (0,0)↔(4,1); (1,1)↔(2,1); (1,1)↔(3,0); (1,1)↔(4,1); (2,1)↔(3,0); (2,1)↔(4,1); and (3,0)↔(4,1).

In practicing the PCR method, if the series of all 40 possible PCR reactions shown in FIG. 3A were run one by one, and amplification (i.e., the PCR "signal") were observed in the above ten PCR reactions, that would indicate that the taggant represented by the numerical value 01101 was present in the sample being analyzed. However, having to provide such a taggant library of DNA taggants having long nucleotide sequences is disadvantageous for the reasons noted previously, particularly when the number of nucleotides exceeds about 100, and the need for extensive encoded information causes the library to become large.

In addressing this problem, the Applicant has discovered that by using smaller DNA fragments that mathematically constitute what is known as a combinatorial cover, the same PCR network graph information can be obtained as would be provided by using a longer DNA taggant. To understand this discovery, consider the set M as being a fixed collection of table-mers DNA_TC(n,q,t). An s-DNA combinatorial cover of M is a collection of double-stranded WC duplex concatenations of s table-mers taken from M that yield exactly all the same positive PCR reactions that exist for the entire taggant library TAG(n,q,nt) for M. A DNA sequence in an s-DNA cover is called a "covering strand" in this disclosure. Additionally, since the length of such a covering strand is s·t base pairs, the s-DNA cover of M is denoted herein as a COV_DNA(n,q,st) of M. COV_DNA(n,q,st) of M may also be referred to as an s-DNA cover of the taggant library TAG(n,q,nt) constructed from M.

By using DNA combinatorial covers of idealized DNA taggant libraries, "virtual taggants," also known herein as ComDTags, can be constructed. These combinatorial DNA taggants behave exactly like longer taggants in the library with respect to their PCR signal. (Thus the ComDTags are "virtual" in the sense that they simulate longer idealized taggants of the taggant library.) Thus, for TAG(n,q,nt), instead of having to painstakingly construct $q^n$ taggants, and having the problems of high cost and low yield, one can construct approximately $q^s$ strands in COV_DNA(n,q,st). The same results as when using a taggant from the library can be obtained by algorithmic mixing to make the ComDTags. This method provides a reduction in taggant cost on the order of $q^{n-s}$. For example, with n=10, q=2, s=3, the reduction is $2^{10-3}$, i.e., approximately 100 fold. Moreover, the physical construction of long DNA taggant sequences when n·t is greater than 200 is cost prohibitive, and virtually impossible if n·t is greater than 250. Thus, to get massive amounts of data storage capabilities, the combinatorial cover COV_DNA(n,q,st) must be used.

Continuing with the use of the TAG(5,2,50) of Table 2 constructed from the table-mers of Table 1 as an example, let C be a COV_DNA(5,2,30) 3-cover. The four covering strands $cs_1$, $cs_2$, $cs_3$ and $cs_4$ in C that appear below in Table 3 together constitute a virtual ComDTag taggant for the actual taggant that appears in FIG. 1, which is the taggant representing the numerical value 01101. The table-mers (shown in Table 3 with their respective ordered pair references) which form the covering strands of Table 3 have been selected according to the principles of combinatorial mathematics, specifically to provide the same PCR signal response as the full length five bit taggant of FIG. 1. The use of this combinatorial DNA taggant in lieu of the taggant of FIG. 1 will now be explained in detail, using a hypothetical example, with reference also to FIG. 2.

(0,0), (1,1), (2,1), (3,0), and (4,1), with those five table-mers being used are primers for the PCR. (However, the remaining PCR reactions may need to be run to verify that no other DNA taggants from library are present in applications where multiple products have been labeled by multiple taggants.) The "virtual" aspect of the collection of the four covering strands can be observed in FIG. 4. Each of the four covering strands gives rise to three positive PCR reactions; so when the PCR technique is used, if the four covering strands are present (as would be the case when testing an authentic object A above), those reactions will occur.

For example, $cs_3$ has positive PCR reactions for the primer pairs in the triangle (2,1), (3,0), (4,1), the lines of which are marked with the shorter dashes ( — — ). More specifically, when a PCR reaction is run with the primer pair (2,1) and (3,0), the left two bits of $cs_3$ consisting of (2,1)(3,0) will be amplified. When a PCR reaction is run with the primer pair (3,0) and (4,1), the right two bits of $cs_3$ consisting of (3,0)(4,1) will be amplified. When a PCR reaction is run with the primer pair (2,1) and (4,1), the entire $cs_3$ strand will be amplified. In all cases, these PCR reactions produce amplification, i.e. increased DNA concentrations that can be detected by the aforementioned known analytical methods. It can be seen that it is not necessary to the PCR reactions reproduce the entire cover strand for them to provide meaningful data.

In like manner, $cs_1$ has positive PCR reactions for the primer pairs in the triangle (0,0), (1,1), (2,1), the lines of which are shaded with circular dots; $cs_2$ has positive PCR reactions for the primer pairs in the triangle (0,0), (1,1), (4,1), the lines of which are shaded with square dots; and $cs_4$ has positive PCR reactions for the primer pairs in the

TABLE 3

Covering strands for the DNA taggant of FIG. 1, a COV_DNA(5, 2, 30) 3-cover shown as WC duplexes.

```
         (0, 0)      (1, 1)      (2, 1)
cs₁ = 5'CGTCCATCGT CGCAAGCTGA AGTGGATGCG3'   (SEQ ID NO: 45)
      3'GCAGGTAGCA GCGTTCGACT TCACCTACGC5'
                  ● ● ● ● ● ● ● ● ● ● ● ● ● ● ● ●

(0, 0)      (1, 1)      (4, 1)
cs₂ = 5'CGTCCATCGT CGCAAGCTGA TCGGAGTGCT3'   (SEQ ID NO: 46)
      3'GCAGGTAGCA GCGTTCGACT AGCCTCACGA5'
                  ■ ■ ■ ■ ■ ■ ■ ■ ■ ■ ■ ■ ■ ■ ■ ■

(2, 1)      (3, 0)      (4, 1)
cs₃ = 5'AGTGGATGCG TCGGTAAGCG TCGGAGTGCT3'   (SEQ ID NO: 47)
      3'TCACCTACGC AGCCATTCGC AGCCTCACGA5'
                  — — — —

(0, 0)      (1, 1)      (3, 0)
cs₄ = 5'CGTCCATCGT CGCAAGCTGA TCGGTAAGCG3'   (SEQ ID NO: 48)
      3'GCAGGTAGCA GCGTTCGACT AGCCATTCGC5'
                  ▬▬▬  ▬▬▬
```

Referring to FIG. 2, a set of ComDTags, which may include the ComDTag of Table 3, is prepared according to steps 110-150. Now suppose a target object A is tagged in step 160 with the ComDTag of Table 3, i.e. the four covering strands $cs_1$-$cs_4$ as an indication of authenticity. Object A is later recovered in step 170, and undergoes whatever routine procedure is required to extract any DNA taggant (if present) therefrom, and to place the DNA taggant in solution so that it can be tested using the PCR technique, which is performed in step 180.

The only PCR reactions that need to be run to detect the presence of the four covering strands are those reactions between the five table-mers that make up those strands, i.e., triangle (0,0), (1,1), (3,0), the lines of which are shaded with the longer dashes. (It is noted that the line between the primers (0,0) and (1,1) appears in three of the four triangles, and is thus partially highlighted by three different markings.)

Figure 4:
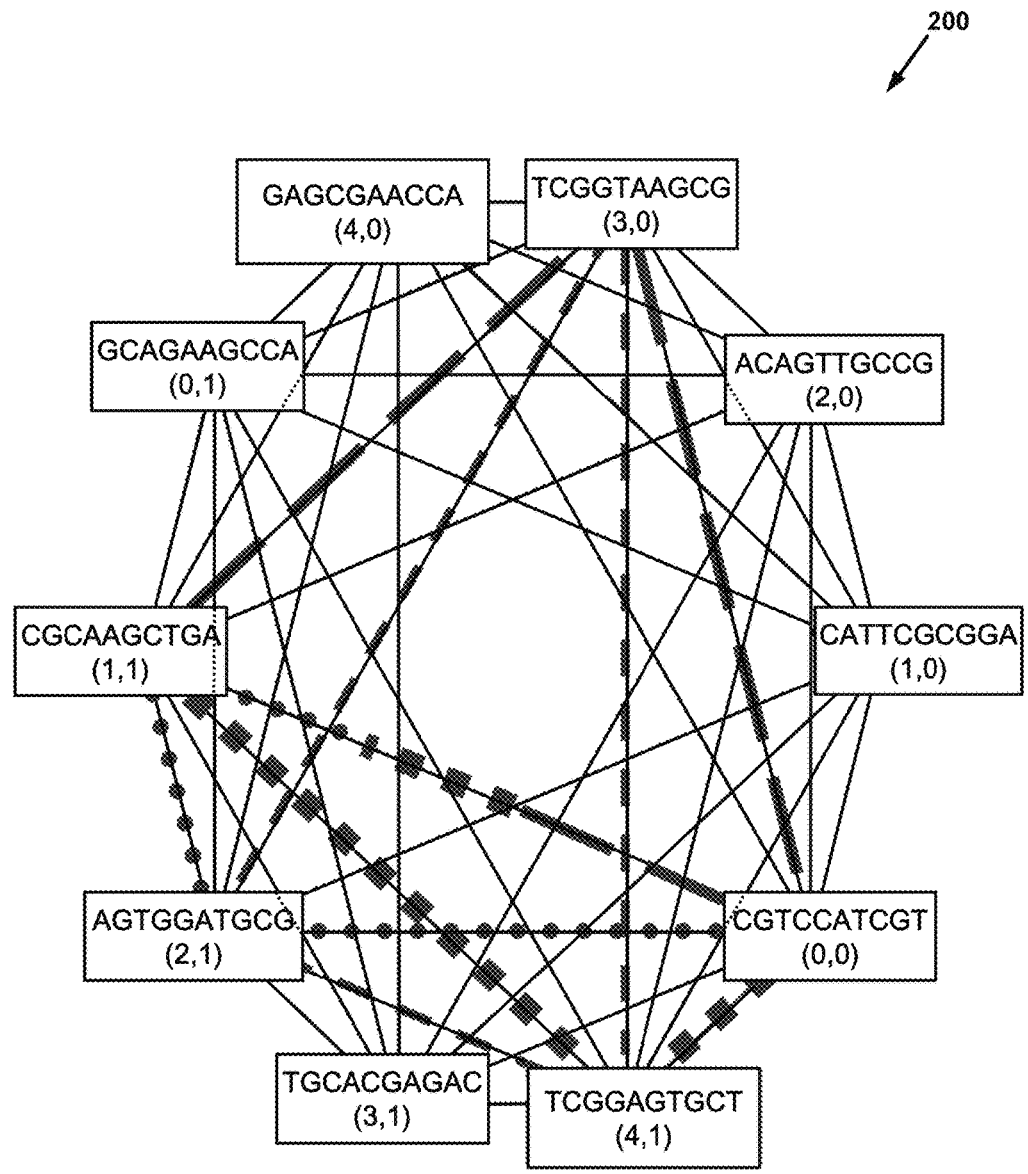
FIG. 4 is a network graph (with positive PCR reactions highlighted) of an actual combinatorial DNA taggant (ComDTag) of the present invention, which is designed to produce the same PCR reactions as the taggant referenced in FIG. 3B (FIG. 4 discloses SEQ ID NOS 1-10, respectively, starting counter-clockwise from the sequence labeled as "(0,0)")

Comparing FIG. 4 to FIG. 3B, it can be observed that $cs_1$, $cs_2$, $cs_3$ and $cs_4$ in total give the same ten distinct positive PCR reactions as does the single longer taggant 10 of FIG. 1 that they cover. This advantageous result is from the Applicant's use of combinatorial mathematics to design the cover strands. In designing the covering strands, first the table-mers present in a given idealized taggant that is to be simulated by the collection of cover strands that make the actual ComDTag are identified. Referring again to FIGS. 1 and 3B as an example, the five table-mers 224 of the taggant 10 are identified. The positive PCR reactions 222 between them are then identified using the network graph 200. The minimum number of cover strands are then identified, such that the combinations of table-mers in those cover strands will cover all of the required PCR reactions. Referring to Table 3 and FIG. 4, it can be seen that the table-mers in the cover strands are chosen such that all the desired PCR reactions that would occur in the full length idealized taggant are covered. In other words, cover strand $cs_1$ contains the table-mers of bits 0, 1, and 2; cover strand $cs_2$ contains the table-mers of bits 2, 3, and 4; cover strand $cs_3$ contains the table-mers of bits 0, 1, and 4; and cover strand $cs_4$ contains the table-mers of bits 0, 1, and 3. Accordingly, all of the PCR reactions that occur between the table-mer primers of all bit pairs, i.e., 0-1, 0-2, 0-3, 0-4, 1-2, 1-3, 1-4, 2-3, 2-4, and 3-4 are covered.

From the perspective of the positive PCR reactions, the single longer idealized taggant 10 of FIG. 1 is indistinguishable from the mixture of the covering strands of Table 3, i.e., the taggant ComDTag. It is much more feasible and cost effective to synthesize four relatively short cover strands than it is to synthesize the single longer taggant strand. It is noted again that for illustrative purposes, the above example uses a shorter taggant, concatenated from shorter table-mers than would be desired for practical applications. Thus the Applicant's method becomes even more enabling and cost effective when longer taggant strands and longer table-mers are used as required in many practical applications.

Additionally, it is not necessary that every taggant in a library has a unique set of covering strands, such that a given taggant library requires the synthesis of covering strands of many times its population. With the covering strands being designed according to combinatorial mathematics, there is overlap in covering strands between taggants. In other words, a single covering strand is used to (partially) cover many different idealized and longer taggants. For example $cs_1$ (partially) covers all idealized taggants corresponding to the bit strings 011xx. For example, the 32 taggants of the library TAG(5,2,50) of Table 2 requires only a total of 32 covering strands, so in this instance there is just a reduction in the length of the strands and not the number of strands. However for the 2187 idealized DNA taggants of length 140 constructed from DNA_TC(7,3,20), wherein q=3, n=7, and t=20, only 187 covering strands, each of length 60 base pairs, need to be produced.

Figure 5:
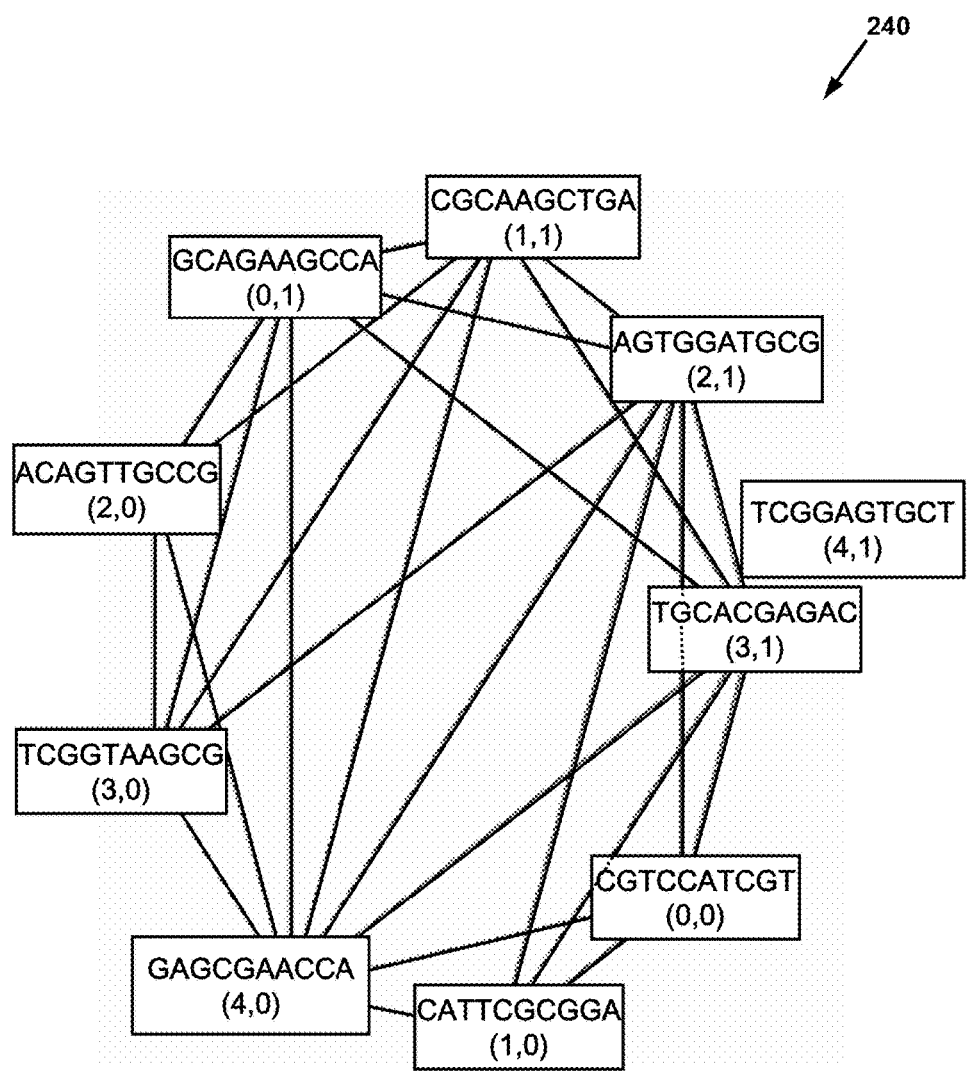
FIG. 5 is a network (sub)graph of the solely positive PCR reactions for a group of four layered taggants, given in FIG. 11, selected from a taggant library (FIG. 5 discloses SEQ ID NOS 1, 9-10, 8, 7, 6, 3-5 and 2, respectively, starting counter-clockwise from the sequence labeled as "(0,0)")

The Applicant's combinatorial DNA taggants, and related methods may be extended to the use of layered taggants. FIG. 5 is a network graph 240 of positive PCR reactions for the group 11000, 00110, 11100 and 11110 of four layered taggants selected from the taggant library TAG(5,2,50) of Table 2. It is noted that theoretically, FIG. 5 would appear the same regardless of whether the four actual TAG(5,2,50) sequences 11000, 00110, 11100 and 11110 of 50 base pairs, or the sixteen (with some repetition possible) covering strands of 30 base pairs in COV_DNA(5,2,30) that covered each of the taggants 11000, 00110, 11100 and 11110, were combined. The covering strands for 11000, 00110, 11100 and 11110 are respectively:

{(012)(110), (034)(100), (134)(100), (234)(000)}
{(012)(110), (034)(010), (134)(110), (234)(110)}
{(012)(111), (034)(100), (134)(100), (234)(100)}
{(012)(111), (034)(110), (134)(110), (234)(110)}

So in total there are 11 distinct covering strands (e.g., (012)(111) and (134)(110) are among repeated strands) for the layer collection of 11000, 00110, 11100,11110. Hence if these taggants were layered simultaneously, there would be an additional reduction in number of covering strands needed to construct the virtual taggant layering. However, if taggants are layered in series over time, there are applications where some covering strands would be necessarily repeated. For example, different ingredients in a drug might have some (not all) similar covering strands and then, when combined as a single drug, similar covering strands would be repeated in the resulting layered taggant for the drug.

As a further demonstration of certain aspects of the invention, a more complex example of the combinatorial DNA taggants and related methods will now be presented. Table 4 is another exemplary table having three values by five positions, and designated DNA_TC(5,2,26), with the table-mers being 26 nucleotides long.

TABLE 4

Exemplary table according to table code DNA_TC(5, 3, 26). All sequences are 26 nucleotides (SEQ ID NOS 49-63, respectively, in order of appearance), read left-to-right and top-to-bottom.

| VALUE0 | position 0 | position 1 | position 2 | position 3 | position 4 |
|---|---|---|---|---|---|
| 0 | TCAACTCTTACCT CAATCTCATACCA | ATCTTCTCCTCCA ATCCATTTCTCAT | CTCTCACTCTCTC ACTCCTTATCAAT | TTCCTACCAAAAC CAAAAACTCCAAT | ATCATCCACTATC CTCTACAACACTT |
| 1 | AACAACCATTCTC CAACCTTCATATT | CATCCTTCTTTCA CTTACACTCACAT | TTTCCAATTCCAA CATAATCCACACA | AAATCCACCTTTT CACAAAACTACCT | CAAAACAAACACT CAACTACACTCTC |
| 2 | TCAAATCACTACC ATCTTTTCCACAA | ACACACACAACA ACACCAAAAATAAA | ACTCACACCAATA TCTACTTTCTCCT | AACCTCCTAATCA CCTCCTATTACAC | TTCACCTCTCTTC CTAAATTCCTCTT |

TABLE 5

Covering strands for the DNA taggant represented by 01121, a COV_DNA(5, 3, 78) 3-cover. All sequences are 26 nucleotides (SEQ ID NOS 49, 62, 58, 56, 62, 58, 49, 55, 56, 55, 62 and 58, respectively, in order of appearance), read left-to-right and top-to-bottom.

| | (01234) | (01211) |
|---|---|---|
| (034)(021) | TCAACTCTTACCT CAATCTCATACCA | AACCTCCTAATCA CCTCCTATTACAC | CAAAACAAACACT CAACTACACTCTC |
| (234)(121) | TTTCCAATTCCAA CATAATCCACACA | AACCTCCTAATCA CCTCCTATTACAC | CAAAACAAACACT CAACTACACTCTC |
| (012)(011) | TCAACTCTTACCT CAATCTCATACCA | CATCCTTCTTTCA CTTACACTCACAT | TTTCCAATTCCAA CATAATCCACACA |
| (134)(121) | CATCCTTCTTTCA CTTACACTCACAT | AACCTCCTAATCA CCTCCTATTACAC | CAAAACAAACACT CAACTACACTCTC |

Figure 6A:
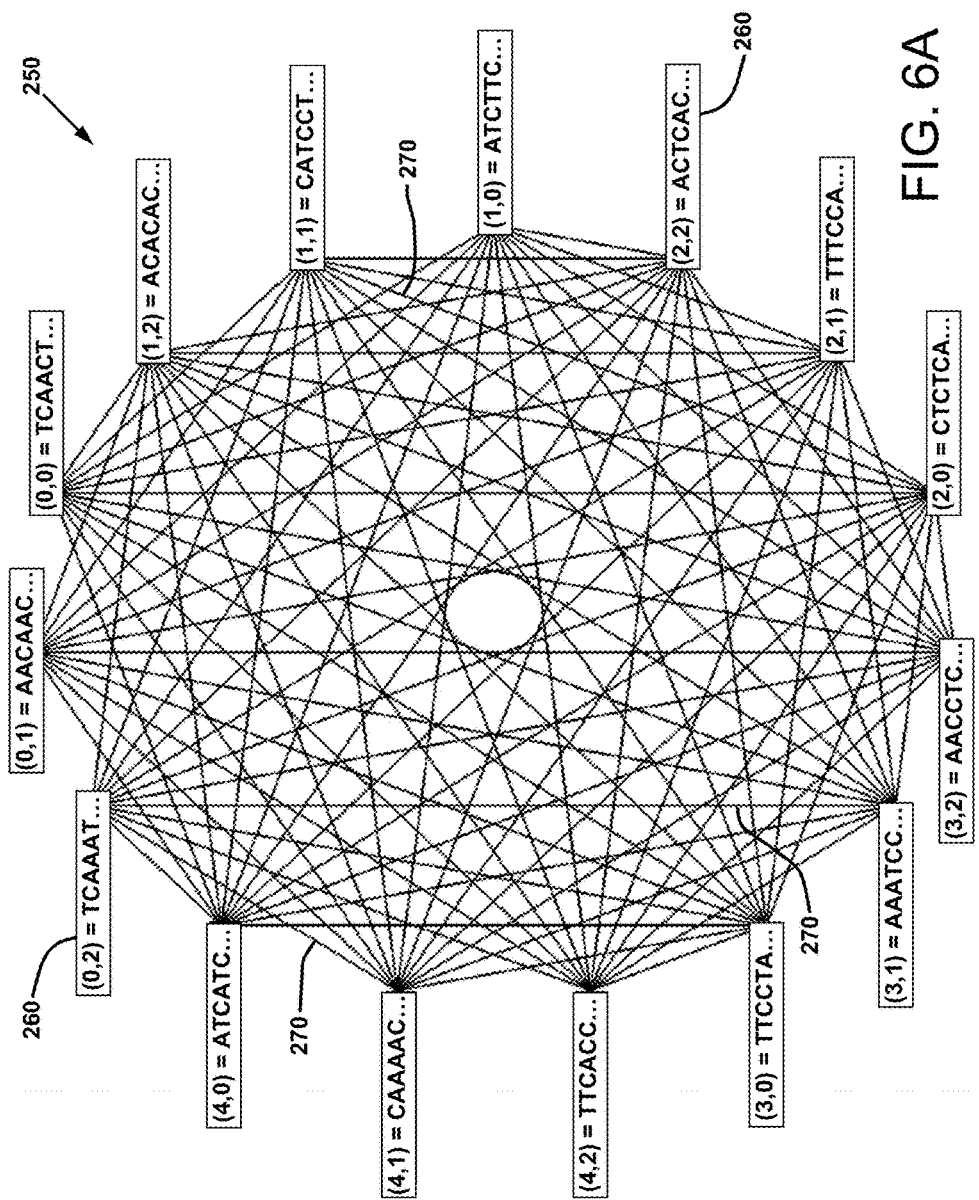
FIG. 6A is a network graph of all possible PCR reactions for a more complex combinatorial DNA taggant example that may be used according to the method depicted in FIG. 2.
Figure 6B:
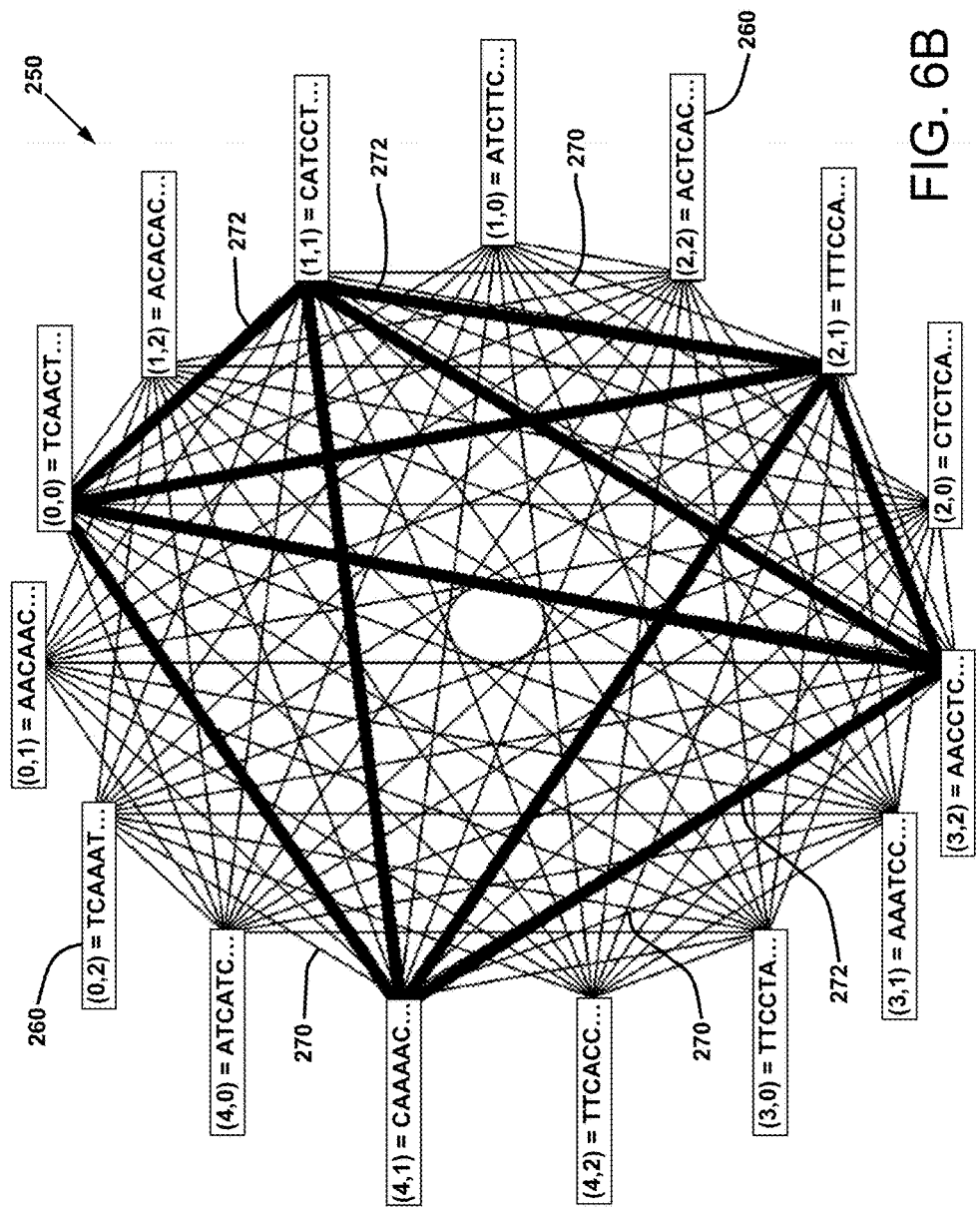
FIG. 6B depicts the network graph of FIG. 6A, modified to identify the set of positive PCR reactions for a specific and idealized DNA taggant represented by a particular alpha-numeric value.

From the table-mers in Table 4, a taggant library TAG(5, 3,130) (not shown) may be created having $3^5=243$ distinct taggants. As noted previously, for a general taggant library TAG(n,q,n·t), there are $n(n-1)q^2/2$ primer pairs of table-mers, and thus the same number of distinct PCR reactions with each taggant being positive for $n(n-1)/2$ of them. In this instance, n=5 and q=3, so there are 90 distinct PCR reactions to perform with any given taggant being positive for 10 of them. Although ninety reactions may appear to be a substantial number, current real time PCR technology, such as that of the aforementioned Stratagene 3000 MX Pro PCR apparatus enables the performance of up to 96 simultaneous reactions. A network graph may be constructed as described previously. FIG. 6A is the network graph depicting the fifteen table-mers 260 of Table 4 and the 90 distinct PCR reactions 270. Referring also to FIG. 6B, the set of bold lines 272 denotes the set of positive PCR reactions for the DNA taggant (SEQ ID NO: 64)
TCAACTCTTACCTCAATCTCATACCA

CATCCTTCTTTCACTTACACTCACAT

TTTCCAATTCCAACATAATCCACACA

AACCTCCTAATCACCTCCTATTACAC

CAAAACAAACACTCAACTACACTCTC represented by 01121. (In graph theoretical terms, this collection of bold edges is called a n-clique (5-clique here), because all of the five vertices (5) involved are mutually connected.)

As described previously, a combinatorial cover may be constructed for the taggant library TAG(5,3,130). Let C be a COV_DNA(5,3,78) 3-cover for this library. The four covering strands (034)(021), (234)(121), (012)(011), (134)(121) in C that appear in Table 5 together constitute a virtual ComDTag taggant for the above actual taggant from the taggant library TAG(5,3,130). The encoding method (position string)(value string) relative to a given table is used to encode the identity of a strand. For example (034)(021) is the concatenation of strands (0,0), (3,2) and (4,1). For consistency, (01234)(01121) denotes the collection of strands in Table 2, i.e., the virtual ComDTag for 01121.

Figure 7:
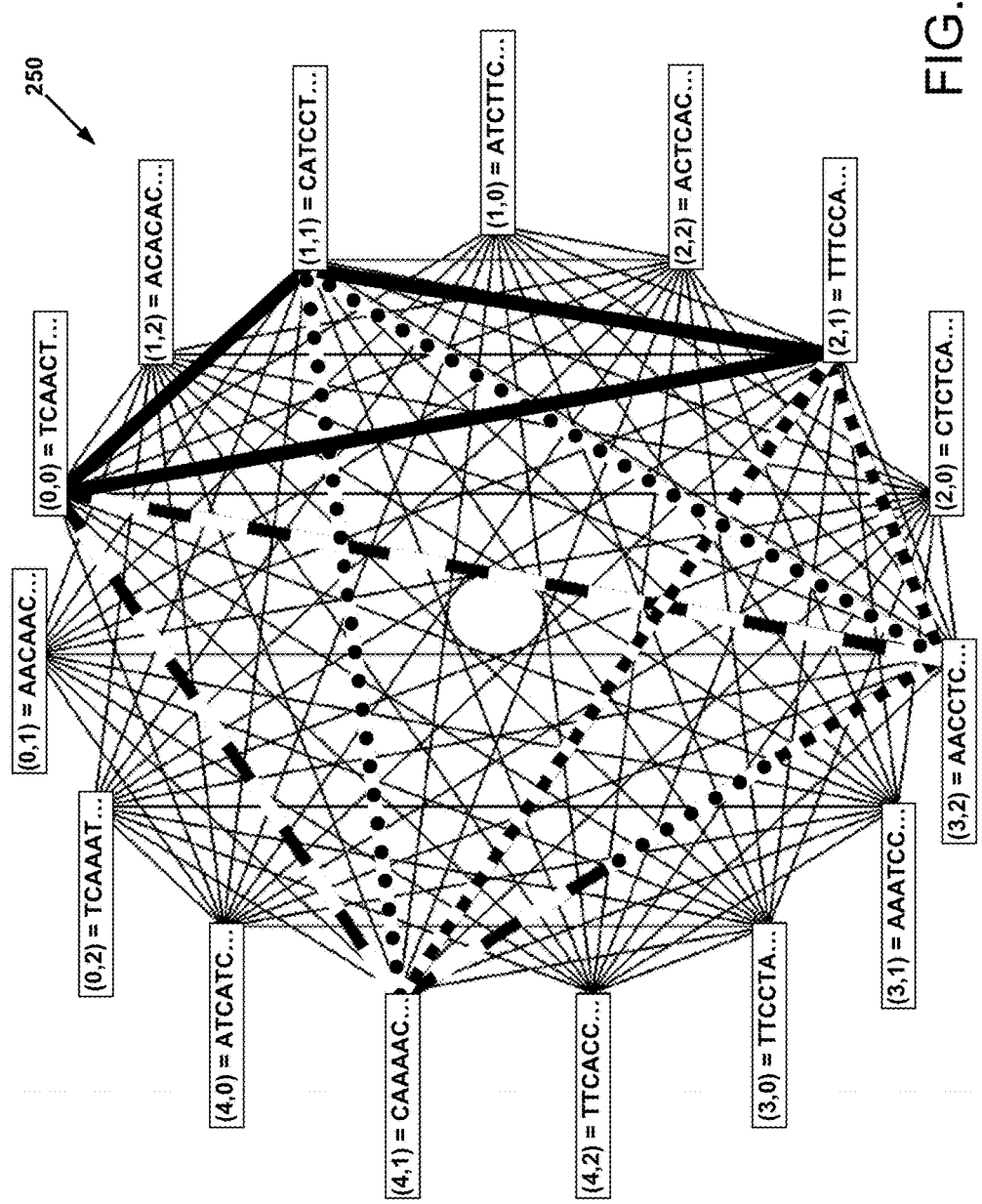
FIG. 7 is a network graph (with positive PCR reactions highlighted) of an actual combinatorial DNA taggant (ComDTag) that is designed to produce the same PCR reactions as the taggant referenced in FIG. 6B.

As described previously, the "virtual" aspect of the collection of the four covering strands can be observed in Table 5. Each of the four covering strands gives rise to three positive PCR reactions. For example, (012)(011) has positive PCR reactions for the primer pairs in the triangle (0,0), (1,1), (2,1) whose lines are solid black. The triangle of edges that are positive for each covering strand (round dots respectively. It is noted that the line between (3,2) and (4,1) appears in three of the four triangles and is thus partially highlighted by three different line formats. Comparing FIG. 7 to FIG. 6B, it can be observed that (034)(021), (234)(121), (134)(121) and (012)(011) in total give the same ten positive PCR reactions as does the single longer taggant that they cover.

Figure 8:
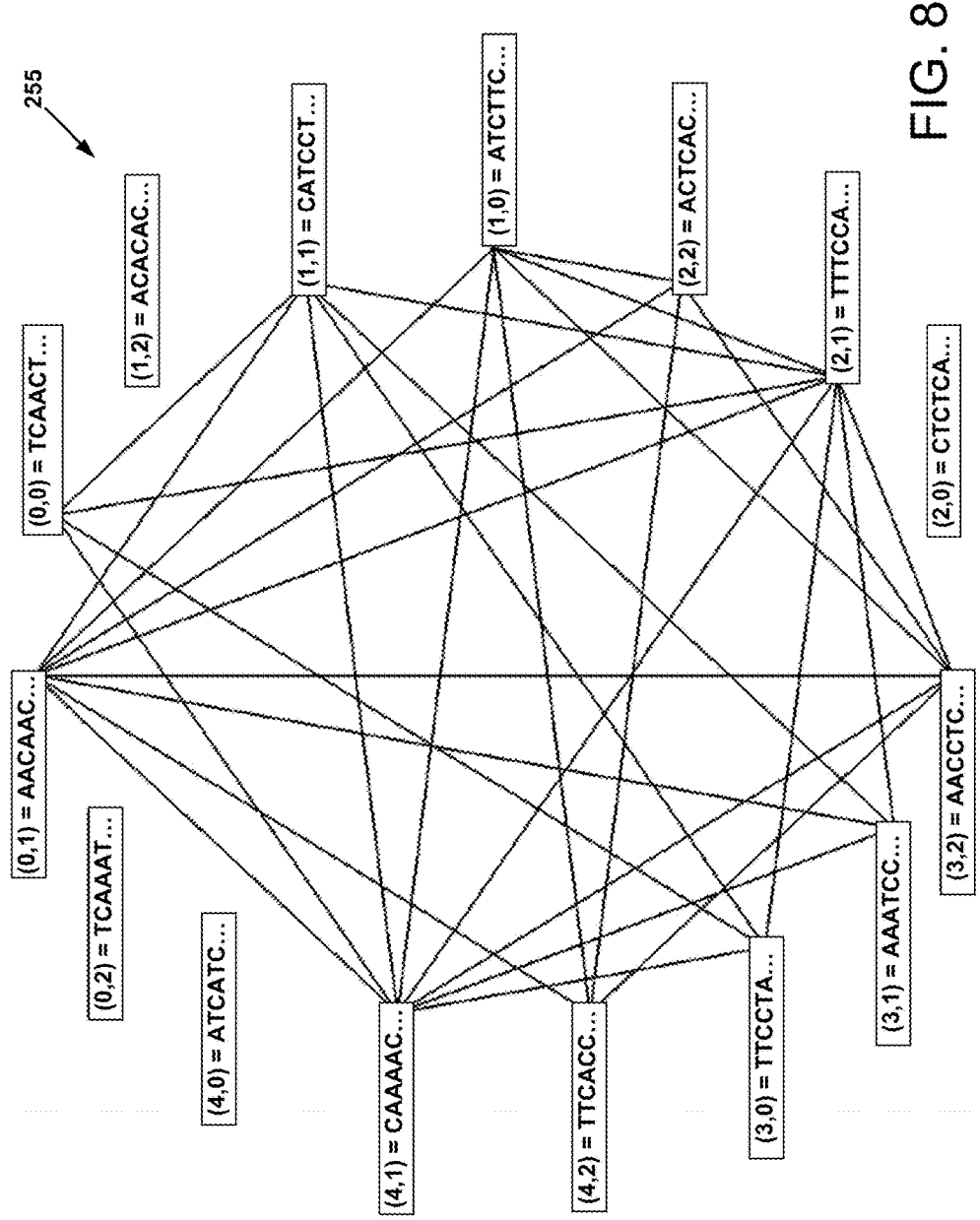
FIG. 8 is an example of a network subgraph that shows only the edges that denote positive PCR reactions for a particular layered combination of four actual combinatorial DNA taggants (ComDTags)

In a graphical representation of PCR reactions, only the edges that denote positive PCR reactions need to be shown. The modified network graph 255 of FIG. 8 gives the positive PCR reactions for the group of four layered ComDTags (01234)(11111), (01234)(01222), (01234)(01121), (01234) (10101) consisting of 16 ComDTag fragments. It has been experimentally verified that FIG. 8 is the same regardless of whether the four actual TAG_LIB(5,3,130) sequences 11111, 01222, 01121, 10101 of 130 base pairs, or the sixteen ComDTag fragment covering strands of 78 base pairs were used in the PCR technique.

Laboratory Demonstration of Combinatorial DNA Taggants and Methods

Proof of principle of the instant DNA taggants and method has been successfully performed, as disclosed in "PCR Nonadaptive Group Testing of DNA Libraries for Biomolecular Computing and Taggant Applications," *Discrete Mathematics, Algorithms and Applications*, Vol. 1, Issue 1 (March 2009), 59-69, Macula, et al. In the study, a set of combinatorial DNA tags was designed and synthesized. A mixture of a small subset of the taggants was prepared and analyzed with the PCR technique as described herein. The laboratory mixture simulated a mixture that could be prepared from a sample of a target that was tagged with the taggant mixture.

Figure 9A:
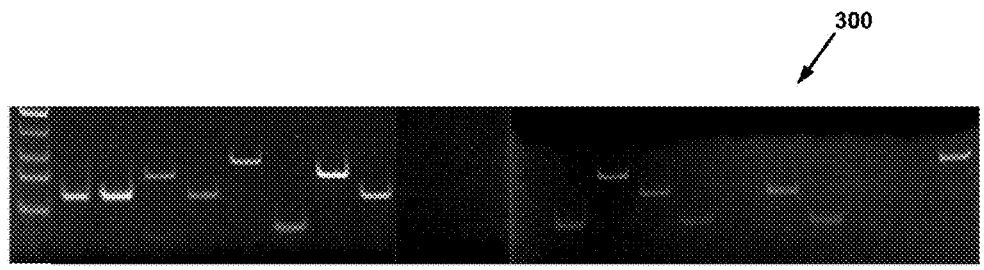
FIG. 9A is a electrophoresis gel image of exemplary combinatorial DNA taggants in a laboratory demonstration of one embodiment of the invention.
Figure 9B:
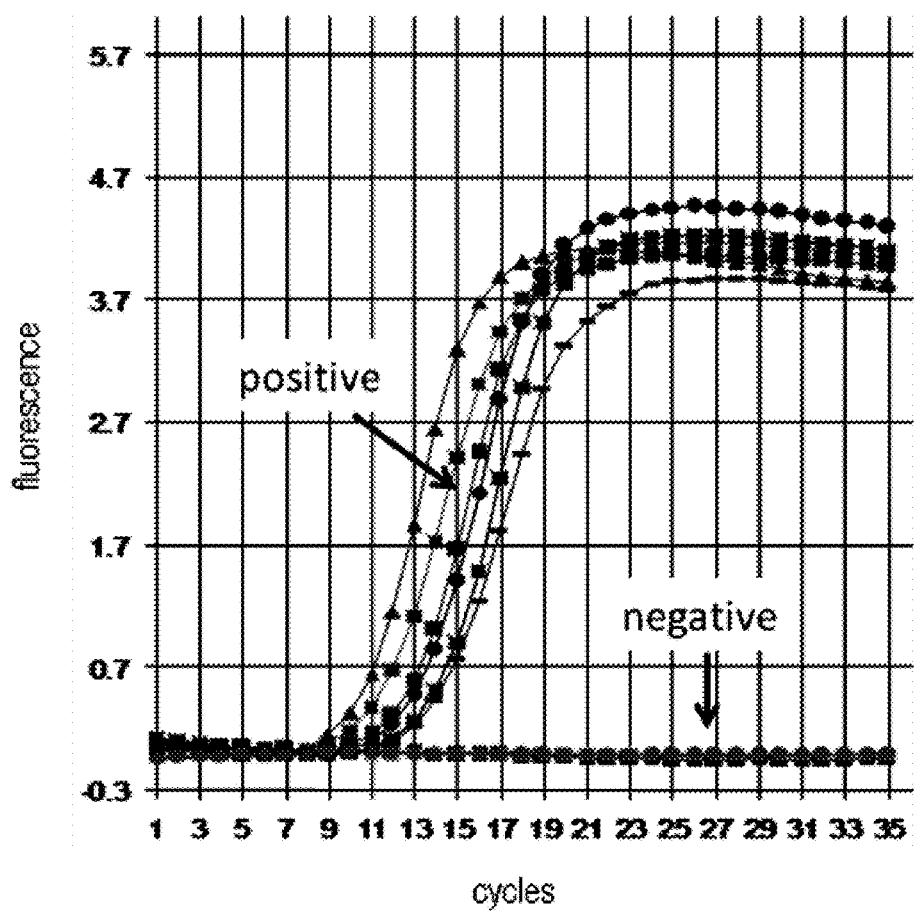
FIG. 9B is a dye based real-time PCR fluorescence image of exemplary combinatorial DNA taggants in a laboratory demonstration of one embodiment of the invention.
Figure 10:
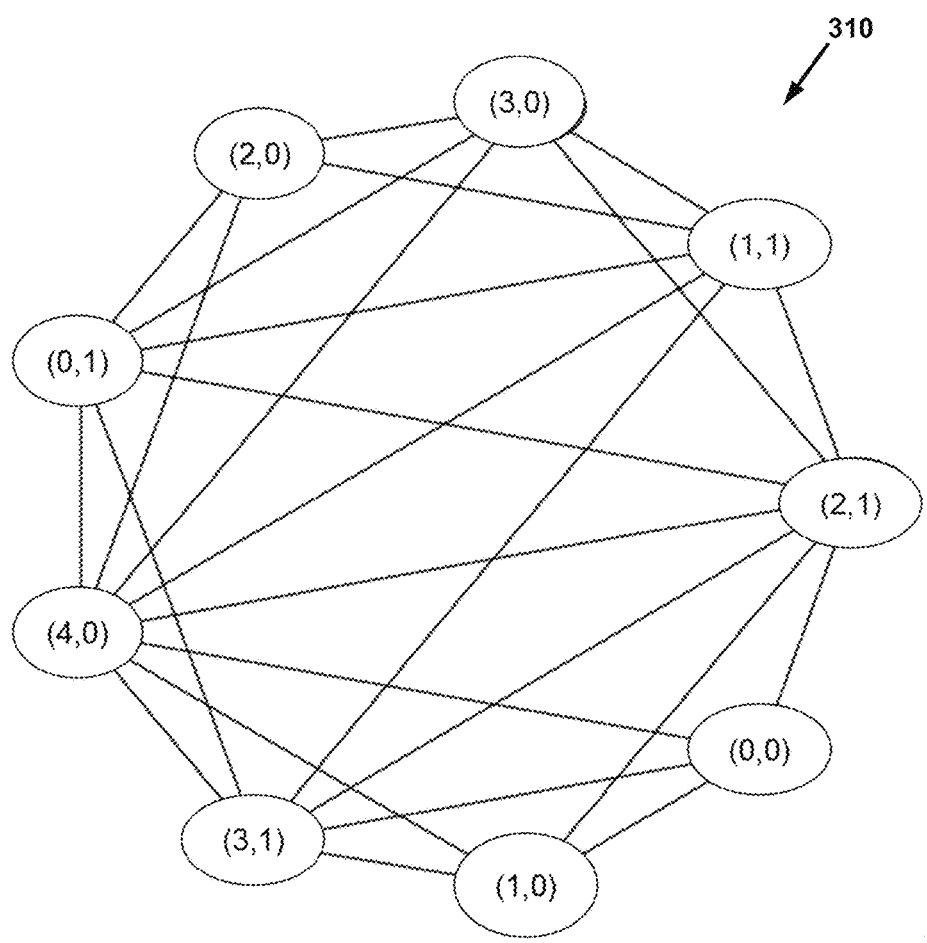
FIG. 10 is a network subgraph prepared in a laboratory demonstration of FIG. 9A, and is essentially the same a FIG. 5 except reference to specific sequences have been removed for simplicity of illustration.

FIG. 9A is a gel electrophoresis image 300 of the combinatorial DNA taggants that were amplified using the PCR method. The PCR data from the image 300 of FIG. 10 was analyzed and interpreted mathematically as the network graph 310 of FIG. 10. Mathematical methods were then used to decompose the graph 310 into components that represent each of the taggants present, which are shown in FIG. 11. The mathematical decomposition methods correctly identified the four taggants of FIG. 10. This experiment simulated a complex real-world use of layered taggants, such as the output of a four step drug production protocol, i.e. using four layered taggants to track and trace a drug product and process.

To get usable layerable and decodable ComDTags, a computer generates the ComDTags to be layered so that they can be decoded by the unique n-clique method discussed below where n is the number of digit positions in the idealized DNA taggant. The given unique n-clique decoding method is a generalization of "edge representative decoding" that appears in the publication of Hwang, F. K., Liu, Y. C., Random Pooling Designs Under Various Structures, *Journal of Combinatorial Optimization* 7, 339-352, 2003.

Let the term positive PCR network graph as used herein denote the collection of solely positive PCR reactions.

A standard computer search algorithm ensures that each n-clique corresponding to a given ComDTag in a layered collection of ComDTags has at least one edge, E, in the positive PCR network graph such that E is a member of one and only one n-clique subgraph of the positive PCR network graph.

Note that every ComDTag always corresponds to a n-clique subgraph of positive PCR network graph, but not necessarily vice-versa. There can be n-clique subgraphs in the positive PCR network graph that do not correspond to a ComDTag in the layered collection of ComDTags that gives rise to the PCR signal represented by positive PCR network graph.

The unique n-clique method that is now described identifies the n-cliques that do correspond to ComDTags.

The unique n-cliques method operates on positive PCR network graph by searching over its edges for those contained in a unique n-clique. If an edge is a member of a unique n-clique in the PCR graph, then that unique n-clique represents a ComDTag. Note, an n-clique may contain several unique edges and this redundancy give the unique n-clique method considerable experimental error-correcting capability.

Since only unique n-cliques are taken, unique n-clique algorithms never mis-identify a non-ComDTag (in the absence of experimental error). It should be noted that since false positives experimental PCR error introduce more (but false) edges in the positive PCR network graph, these added (but false) edges can only increase the number of n-cliques present. Hence false positives cannot lead to the misidentification of a ComDTag. False positives can cause some ComDTags not to be identified, but what partial information is obtained in the presence of false positive experimental error is still correct, albeit perhaps partial, decoding. This is a very attractive aspect of the Applicant's method, as false positives are more likely than false negatives in PCR applications.

For example, recall from FIG. 3B and FIG. 4 that each ComDTag (in that example displayed) corresponds to a 5-clique in the PCR graph. FIG. 5 is the positive PCR network graph signal received from a layered mixture of the four taggants (01234)(11000), (01234)(00110), (01234)(11100) and (01234)(11110) selected from the taggant library TAG(5,2,50) of Table 2.

Applying the unique 5-clique method to FIG. 5 gives that:
edge (0,1) ↔ (2,0) is unique for 5-clique (01234)(11000),
edge (0,0) ↔ (1,0) is unique for 5-clique (01234)(00110),
edge (2,1) ↔ (3,0) is unique for 5-clique (01234)(11100), and
edge (0,1) ↔ (3,1) is unique for 5-clique (01234)(11110).

Thus all four of the layered taggants have been successfully decoded in this case.

In the above experimental study, gel electrophoresis was used to provide data on the amplification of the DNA taggants. Other analytical techniques are also suitable, such as those previously identified herein. Such methods and instruments can reliably provide the information needed to perform the mathematical algorithms used in the invention in a fast and cost effective manner.

Alternative and Exclusively Binary Combinatorial DNA Taggants and Method

In accordance with the invention, alternative combinatorial DNA taggants and methods are provided. These taggants and methods will now be described through the use of illustrative examples thereof.

In a second method of representing solely binary sequences in DNA, one may begin with a fixed set of n relatively short t-mers of ssDNA and their reverse complements. An exemplary set is shown in Table 6 below, wherein n=4 and t=22.

In the general case of this method, a total of n(n−1)/2 concatenations of the strands and their complements may be made. This enables the encoding of bit strings up to a length of n(n−1)/2. Table 7 depicts the relationship between the number of table strands and complements, the number of encoding bit register strands, and the number of distinct bit strings that can be encoded using the table strands and their reverse complements. For the strands of Table 6, six concatenations of the strands are possible, as shown in Table 8.

TABLE 6

Exemplary table of short single DNA strands (SEQ ID NOS 65-68, respectively, in order of appearance) and their reverse complements (SEQ ID NOS 69-72, respectively, in order of appearance), all shown in 5' → 3' order.

| | | | |
|---|---|---|---|
| strand 1 | GCGTGATAGTTACTTAACGATC | complement 1 | GATCGTTAAGTAACTATCACGC |
| strand 2 | ATCAACATTGCTATACTCACTG | complement 2 | CAGTGAGTATAGCAATGTTGAT |
| strand 3 | TGTTCTGTACGAGCTAGATTAT | complement 3 | ATAATCTAGCTCGTACAGAACA |
| strand 4 | CACATCATTCAACAATCTGAGA | complement 4 | TCTCAGATTGTTGAATGATGTG |

TABLE 7

Relationship between number of table strands and complements, number of encoding bit register strands, and number of distinct bit strings that can be encoded.

| n = number of table strands and complements of length t | N = number of encoding bit register strands of length 2t  N = n(n − 1)/2 | B = number of distinct bit strings that can be encoded  B = $2^N$ |
|---|---|---|
| 2 | 1 | 2 |
| 4 | 6 | 64 |
| 6 | 15 | 32768 |
| 8 | 28 | 268435456 |
| 10 | 45 | $3.51844 \times 10^{13}$ |
| 15 | 105 | $4.05648 \times 10^{31}$ |
| 20 | 190 | $1.56928 \times 10^{57}$ |

TABLE 8

Example of bit register encoding using ssDNA strands of Table 6.

bit register encoding strands
(concatenations of t-mers and complements)
(SEQ ID NOS 73-78, respectively, in order of appearance)

| | strand 1 t-mer | strand 2 reverse complement |
|---|---|---|
| encoder bit register 1 | GCGTGATAGTTACTTAACGATC | CAGTGAGTATAGCAATGTTGAT |
| encoder bit register 2 | strand 1 t-mer  GCGTGATAGTTACTTAACGATC | strand 3 reverse complement  ATAATCTAGCTCGTACAGAACA |
| encoder bit register 3 | strand 1 t-mer  GCGTGATAGTTACTTAACGATC | strand 4 reverse complement  TCTCAGATTGTTGAATGATGTG |
| encoder bit register 4 | strand 2 t-mer  ATCAACATTGCTATACTCACTG | strand 3 reverse complement  ATAATCTAGCTCGTACAGAACA |
| encoder bit register 5 | strand 2 t-mer  ATCAACATTGCTATACTCACTG | strand 4 reverse complement  TCTCAGATTGTTGAATGATGTG |
| encoder bit register 6 | strand 3 t-mer  TGTTCTGTACGAGCTAGATTAT | strand 4 reverse complement  TCTCAGATTGTTGAATGATGTG |

TABLE 9

Bit register readers to read encoding strands of Table 8.

| | bit register readers: corresponding unique positive primer pair | |
|---|---|---|
| reader bit register 1 | Strand 1 | Strand 2 |
| reader bit register 2 | Strand 1 | Strand 3 |
| reader bit register 3 | Strand 1 | Strand 4 |
| reader bit register 4 | Strand 2 | Strand 3 |
| reader bit register 5 | Strand 2 | Strand 4 |
| reader bit register 6 | Strand 3 | Strand 4 |

For the strands of Table 6, six concatenations of the strands are possible, as shown in Table 8. It can be seen that by using this method, any binary sequence (bit string) of length six can be encoded (or written) by mixing corresponding encoding strands that correspond exclusively to the bit registers with value 1. Then, as shown by Table 9, the encoded bit string can be decoded (or read) by exposing the mixture to six PCR reactions. Each PCR reaction may be primed by the unique corresponding primer pairs, wherein the left primer may be the first part of the encoding strand and the right primer may be the complement of the second part of the encoding strand. (In this case, the PCR reaction occurs only at the right ends of the strands in solution in the first PCR cycle; and in subsequent PCR cycles, the PCR reaction can occur at both ends of the strands. It will be apparent that alternatively, the primer pair may be chosen such that the left primer may be the complement of the first part of the encoding strand and the right primer may be the complement of the second part of the encoding strand.) To facilitate the decoding/reading, the PCR reactions may be dye-based.

Figure 12:
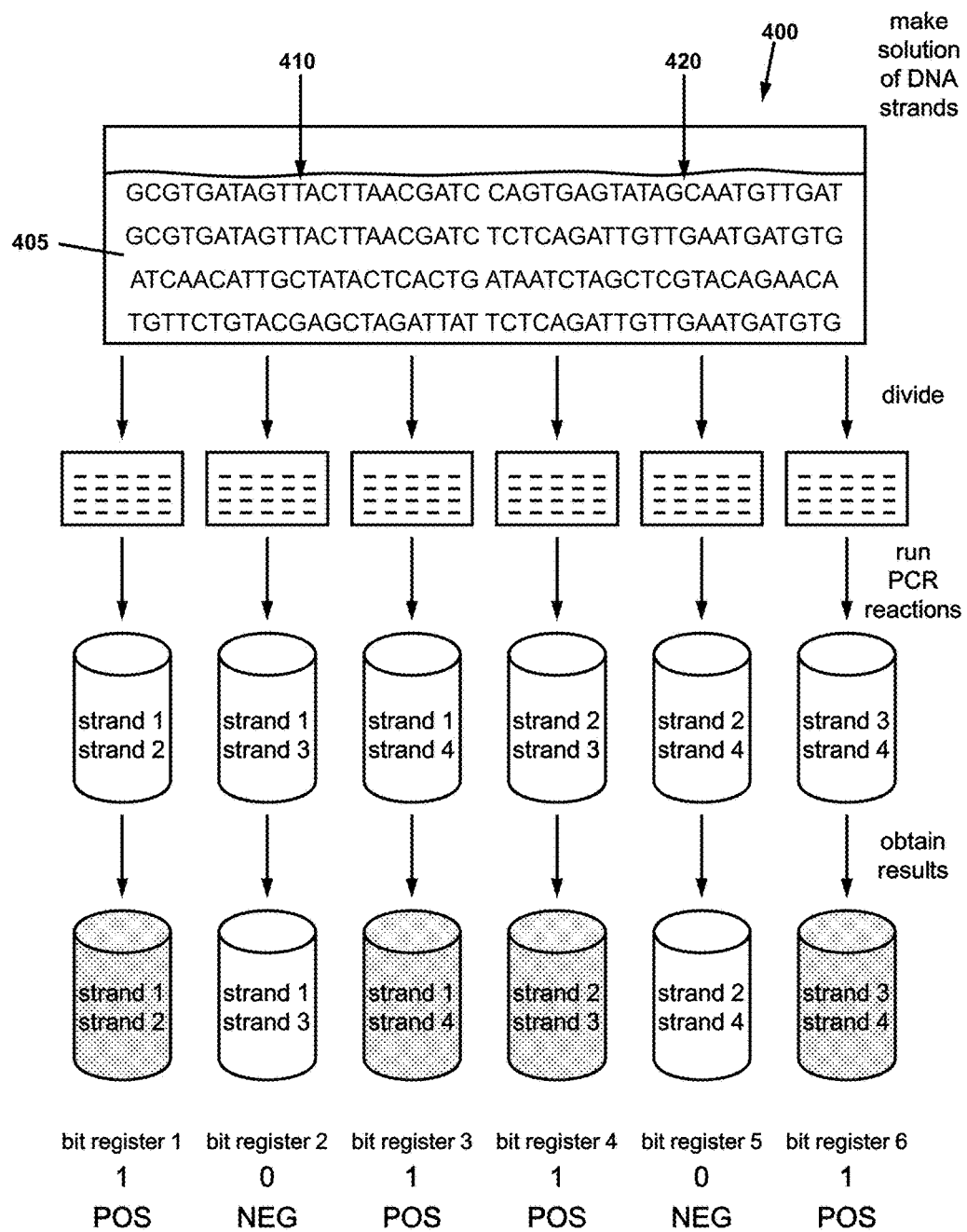
FIG. 12 depicts an example of a method of encoding an alpha-numeric bit string by mixing pairs of concatenated strands of DNA (SEQ ID NOS 73, 75-76 and 78, respectively, in order of appearance) that represent bit registers, the method useable with dye-based PCR.

FIG. 12 depicts an example in which the bit string 101101 is encoded by mixing the concatenated strands of encoder bit register 1, encoder bit register 3, encoder bit register 4, and encoder bit register 6 into a single liquid solution. This is done according to the general principle of this method, which is that for each entry in the bit string, the particular bit encoding concatenated strand is included in the solution if and only if the value in the given entry is a 1. Thus for the bit string 101101, the first, third, fourth, and sixth bits are 1's, and therefore, the concatenated strands for encoder bit registers 1, 3, 4, and 6 of Table 8 are included in the solution. Conversely, the second and fifth bits are 0's, and therefore, the concatenated strands for encoder bit registers 2 and 5 of Table 8 are absent from the solution.

Referring to FIG. 12, and in the method 400 depicted therein, the four ssDNA strands representing encoder bit registers 1, 3, 4, and 6 are placed in a solution 405. The solution 405 is then divided into six aliquots, or six samples are taken from the solution 405. PCR reactions are then run, wherein the respective samples are reacted with each primer pair of register readers of Table 9. Since each register reading primer pair will only react positively with its corresponding concatenated encoder strand, any bit string can be encoded by simply mixing together all the encoding register strands that correspond to a 1 in the bit string that is to be encoded. It can be seen from FIG. 12 that positive PCR reactions (i.e. amplification) occurs where the encoder strands are present. As noted previously, the PCR reactions may be dye-based, so that a positive reaction is indicated by a color change that can be visually observed or optically read.

In accordance with the invention, the combination of strands representing a particular bit string may be used as a combinatorial DNA taggant, or as a layered combinatorial DNA taggant. Using the strands of Table 6 and Table 8, and the bit string 101101 again as an example, the solution of FIG. 12 containing the encoder bit registers 1, 3, 4, and 6 may be applied to a target object, or the ssDNA of encoder bit registers 1, 3, 4, and 6 may be individually applied in or onto a target object. For a layered taggant, they may be applied at different points of a manufacturing process. Subsequently the target object may be recovered with a need for authentication and/or tracking and tracing. Some of the taggant DNA may be recovered from the object, again placed in solution, divided into six samples, and the six respective PCR reactions run. If a result as shown in FIG. 12 is obtained, authenticity and/or the proper complete tracing through the process would be verified. This method of construction of DNA taggants can be employed in all the aforementioned real world applications, e.g., drugs. Moreover, with this binary encoding, all classical and well established information-theoretic methods of processing binary digital signals can be applied to the interpretation of binary signals generated by the PCR methods described above. Thus individual taggants can be encoded and decoded via classical error-correcting methods, such as those disclosed in F. J. MacWilliams and N. J. A. Sloane, *The Theory of Error-Correcting Codes*, ISBN: 0-444-85193-3, 762 pp., North-Holland Mathematical Library, Volume 16. Publisher: North-Holland, New York, 1998.

Additionally, layered taggants can be encoded and encoded via superimposed and disjunct coding, using methods such as those disclosed in Du, D. Z. and Hwang, F. K., 2000. Combinatorial Group Testing and Its Applications, 2nd ed. World Scientific, Singapore.

The above method is particularly suitable for use with dye-base real-time qPCR detection methods. If a probe based PCR detection method is used, a slightly different encoding method must be used in combination with it. Continuing to build on the previous examples, the ssDNA strands of Table 8 and Table 9 may be augmented with a probe-probe complement pair. Such a complement pair may be, e.g., probe: AAGAGTTGTCATTACTCGAATG (SEQ ID NO: 79) and probe complement: CATTCGAGTAAT-GACAACTCTT (SEQ ID NO: 80).

Table 10 and Table 11 present the respective bit register encoders and bit register readers for this example. It can be seen that the bit register encoders of Table 10 each have the probe complement inserted between the respective t-mer and complement strands. Thus these bit encoders are concatenations of three strands. The t-mer and complement ends of these new strands are exactly the same as for the example of Table 8, and therefore are unique for exactly the same positive PCR reactions previously described. Accordingly, there are exactly the same number of bit encoding strands as before and exactly the same number of distinct bits strings can be encoded.

TABLE 10

Example of bit register encoding using ssDNA strands of Table 6 for use with probe-based PCR detection.

bit register encoding strands
(concatenations of t-mer strands and complements)
(SEQ ID NOS 81-86, respectively, in order of appearance)

| | | | |
|---|---|---|---|
| encoder bit register 1 | strand 1 t-mer GCGTGATAGTTACTTAACGATC | probe complement CATTCGAGTAATGACAACTCTT | strand 2 reverse complement CAGTGAGTATAGCAATGTTGAT |
| encoder bit register 2 | strand 1 t-mer GCGTGATAGTTACTTAACGATC | probe complement CATTCGAGTAATGACAACTCTT | strand 3 reverse complement ATAATCTAGCTCGTACAGAACA |
| encoder bit register 3 | strand 1 t-mer GCGTGATAGTTACTTAACGATC | probe complement CATTCGAGTAATGACAACTCTT | strand 4 reverse complement TCTCAGATTGTTGAATGATGTG |
| encoder bit register 4 | strand 2 t-mer ATCAACATTGCTATACTCACTG | probe complement CATTCGAGTAATGACAACTCTT | strand 3 reverse complement ATAATCTAGCTCGTACAGAACA |
| encoder bit register 5 | strand 2 t-mer ATCAACATTGCTATACTCACTG | probe complement CATTCGAGTAATGACAACTCTT | strand 4 reverse complement TCTCAGATTGTTGAATGATGTG |
| encoder bit register 6 | strand 3 t-mer TGTTCTGTACGAGCTAGATTAT | probe complement CATTCGAGTAATGACAACTCTT | strand 4 reverse complement TCTCAGATTGTTGAATGATGTG |

TABLE 11

Bit register readers to read encoding strands of Table 10.

bit register readers:

| | | | probe (all disclosed as SEQ ID NO: 79) |
|---|---|---|---|
| | corresponding unique positive primer pair | | |
| reader bit register 1 | Strand 1 | Strand 2 | AAGAGTTGTCATTACTCGAATG |
| reader bit register 2 | Strand 1 | Strand 3 | AAGAGTTGTCATTACTCGAATG |
| reader bit register 3 | Strand 1 | Strand 4 | AAGAGTTGTCATTACTCGAATG |

TABLE 11-continued

Bit register readers to read encoding strands of Table 10.
bit register readers:

|  | corresponding unique positive primer pair | | probe (all disclosed as SEQ ID NO: 79) |
|---|---|---|---|
| reader bit register 4 | Strand 2 | Strand 3 | AAGAGTTGTCATTACTCGAATG |
| reader bit register 5 | Strand 2 | Strand 4 | AAGAGTTGTCATTACTCGAATG |
| reader bit register 6 | Strand 3 | Strand 4 | AAGAGTTGTCATTACTCGAATG |

Figure 13:
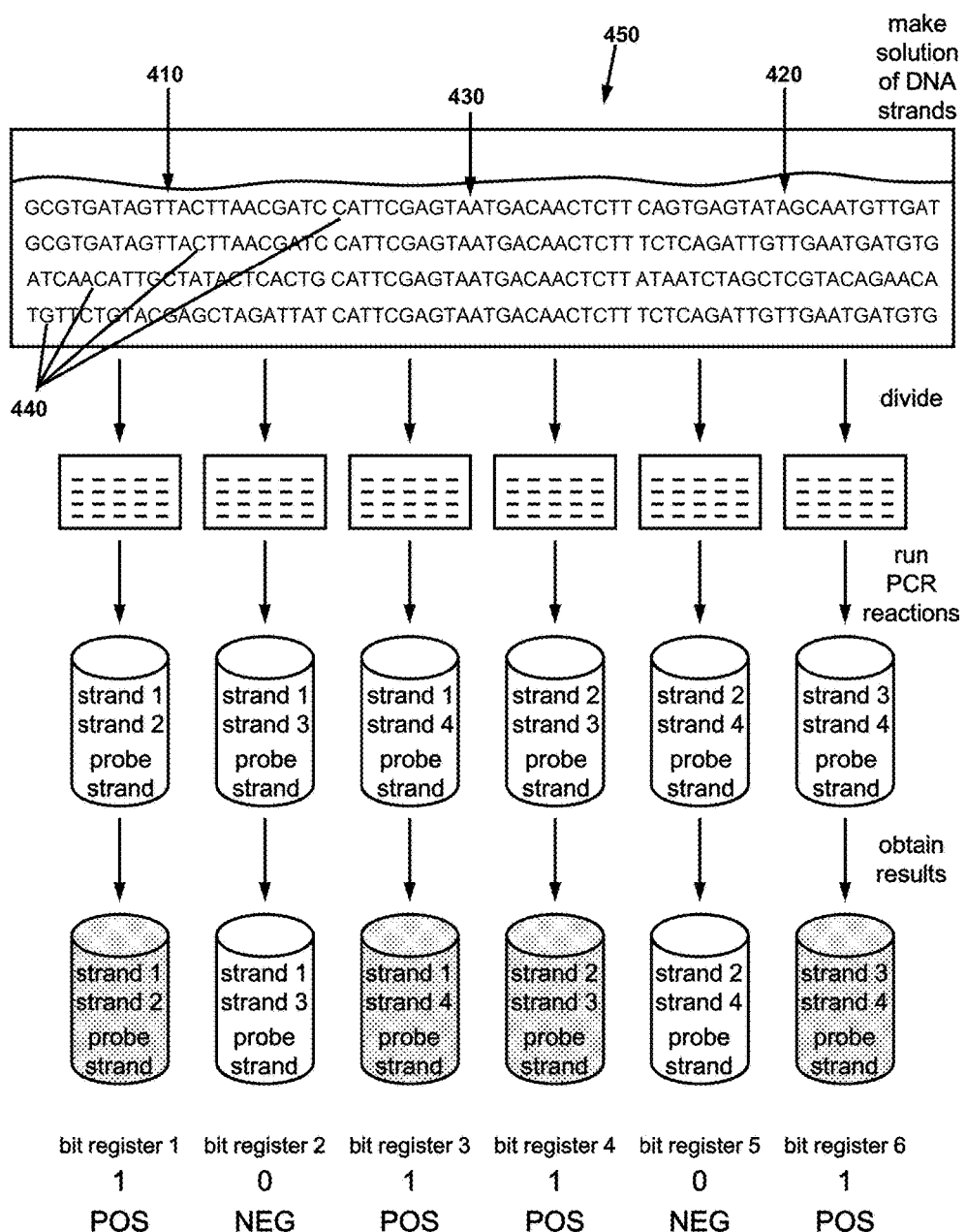
FIG. 13 depicts an example of an alternative method of encoding an alpha-numeric bit string by mixing triples of concatenated strands of DNA (SEQ ID NOS 81, 83-84 and 86, respectively, in order of appearance) which represent bit registers, the method useable with probe-based PCR.

The difference between the two methods is in the method of PCR amplification detection, as illustrated in FIG. 13. In both the method 400 of FIG. 12 and the method 450 of FIG. 13, the bit registers are encoded by the first portions 410 and last portions 420 of the strands.

In the method 400 of FIG. 12, the encoding strands are of length s equal to two times the length of the t-mers, i.e. 44 base pairs in this example. In the method 450 of FIG. 13, the encoding strands are of a length equal to three times (or more) the length of the t-mers, i.e., 66 base pairs in this example.

In the method 400, the amount of increase in doubled stranded DNA that results from PCR amplification is detected by means of a dye, such as e.g., the SYBR Green I asymmetrical cyanine dye. Such dyes are non-specific, and detect any dsDNA that results from amplification.

In the method 450, a probe specifically detects the amplification of the inserted probe sequence 430, which is also amplified. Thus primer-dimer formation (which may occur in the method 400) does not lead to false reads. Moreover, more than one probe sequence 430 may be used. A unique probe sequence 430 may be inserted into each register encoding sequence 440. (In the method 450 of FIG. 13, a common probe sequence 430 was inserted for simplicity of illustration.) Thus this method of detection is highly specific and less prone to error, albeit more expensive due to the need to synthesize longer strands.

As recited previously for the strands of the method 400 of FIG. 12, the combination of the n strands in the method 450 that represent a particular bit string may be used as a combinatorial DNA taggant.

This method of construction of a DNA taggant in 400 and 450 is similar to the ComDTag method discussed above in 100 in that short strands are combined to convey a long signal or sequence. However, methods 400 and 450 are different from method 100 in the way the strands are combined. In methods 400 and 450, each strand in the combination represents a distinct bit register in a longer sequence that has value 1. The strands not in the given combination represent bit registers in a longer sequence with value 0. The method in 100 encodes all q-ary values (0 to q−1) only with the presence of a shorter covering strand (i.e., it doesn't use strand absence to denote a register value). Moreover, method 100 is q-ary and encodes multiple q-ary registers on a single short strand. Methods 400 and 450 are exclusively binary and each strand encodes only one binary register.

Non-DNA Taggants Layered with Covert Combinatorial DNA Taggants

In accordance with the invention, the Applicant's combinatorial DNA taggants may be layered with other non-DNA taggants. The non-DNA taggants may be covert or overt taggants. The non-DNA taggants may be in liquid form, or solid form, such as a powder. In certain embodiments, the solid form taggant may be an up-converting phosphor material, which when irradiated with energy of a specific wavelength, absorbs the energy and re-emits it at a different wavelength. The up-converting phosphor material may emit visible light when excited by long wavelength light. For example, ytterbium/erbium co-doped fluoride is a high efficiency up-converting phosphor that emits strong green fluorescence and relatively weak red fluorescence when excited by 946-970 nm infrared light. Due to their unique properties, up-converting phosphors are used in the fabrication of light-emitting diodes, solid-state lasers, and as ultra-sensitive fluorescent labels in biological detections, such as those disclosed in U.S. Pat. No. 5,674,698, the disclosure of which is incorporated herein by reference.

The Applicant's combinatorial DNA taggants may be blended with an up-converting phosphor material, which may be provided in powder form. One suitable up-converting phosphor material is MicroTagg™, which is manufactured and sold by BrandWatch Technologies of Portland, Oreg. The ComDTags of method 100, 400 or 450 may be in a liquid solution, such that the liquid solution is combined with the up-converting phosphor powder, with the resulting mixture then being dried. An attrition step may be performed if needed to reduce the resulting solid back to flowable powder form.

A taggant comprising one or more of the instant combinatorial DNA taggants and an up-converting phosphor taggant is referred to herein as a phosphorDNA taggant. Such a taggant may be useful as a combination overt-covert taggant. For example, when used, an initial detection and/or authentication may be performed on the overt taggant, i.e. the phosphor powder, which is present on a target object. When irradiated with a particular wavelength, the emitting wavelength is detected, providing an initial fast indication of authenticity. Subsequently, the target object may be further analyzed, wherein the part of the object containing the phosphorDNA taggant is recovered, and at least some of the combinatorial DNA taggant (if present) is placed in solution. The PCR reactions and analysis as described herein are then run, and further determinations of authenticity and tracking and tracing are performed.

Any of the instant combinatorial DNA taggants disclosed herein may be used as layered taggants with a non-DNA taggant, such as an up-converting phosphor. The combinatorial DNA taggants may be made according to the method 100 of FIG. 2, or made as described previously for detection and analysis by the methods 400 and 450 of FIGS. 12 and 13, respectively. For example, using the strands of Table 6 and Table 8, and the bit string 101101 again as an example, the strands of the encoder bit registers 1, 3, 4, and 6 of Table 8 may be mixed with an up-converting inorganic phosphor to produce a specific phosphorDNA taggant.

If a particular ComDTag name used in a phosphorDNA is provided, this specific phosphorDNA may be referred to as phosphorDNA<fragment name(s)>. For example, if ComDTag fragment, encoder bit register 1, abbreviated EBR1, from Table 8 has been used, then it may be referred to as phosphorDNA_EBR1. If a set S of multiple strands, e.g., all four of the fragments use to encode 101101 as described previously, i.e., EBR1, EBR3, EBR4, and EBR6 are used as a layered ComDTag in a phosphorDNA, it may be referred to as phosphorDNA_101101.

However, if each member of a set S of ComDTag fragments is individually used as a tag to create a set of distinct phosphorDNAs, then the set of individual phosphorDNAs may be referred to as S<phosphorDNA>. For example, {EBR1, EBR3, EBR4, EBR6}_phosphorDNA={phosphorDNA_EBR1, phosphorDNA_EBR3, phosphorDNA_EBR4, phosphorDNA_EBR6}.

Thus by mixing the four separate powders in {EBR1, EBR3, EBR4, EBR6}_ phosphorDNA into a single powder called Mix {EBR1, EBR3, EBR4, EBR6}_phosphorDNA, the mixed powder will be indistinguishable from phosphorDNA_101101 in its PCR reactions. One advantage of this method of making the phosphorDNA taggant is that it is significantly easier to dry m distinct DNA strands into m distinct phosphors and then mix the phosphors, as compared to mixing the strands and then drying $2^m$ individual mixtures on phosphors.

Figure 14:
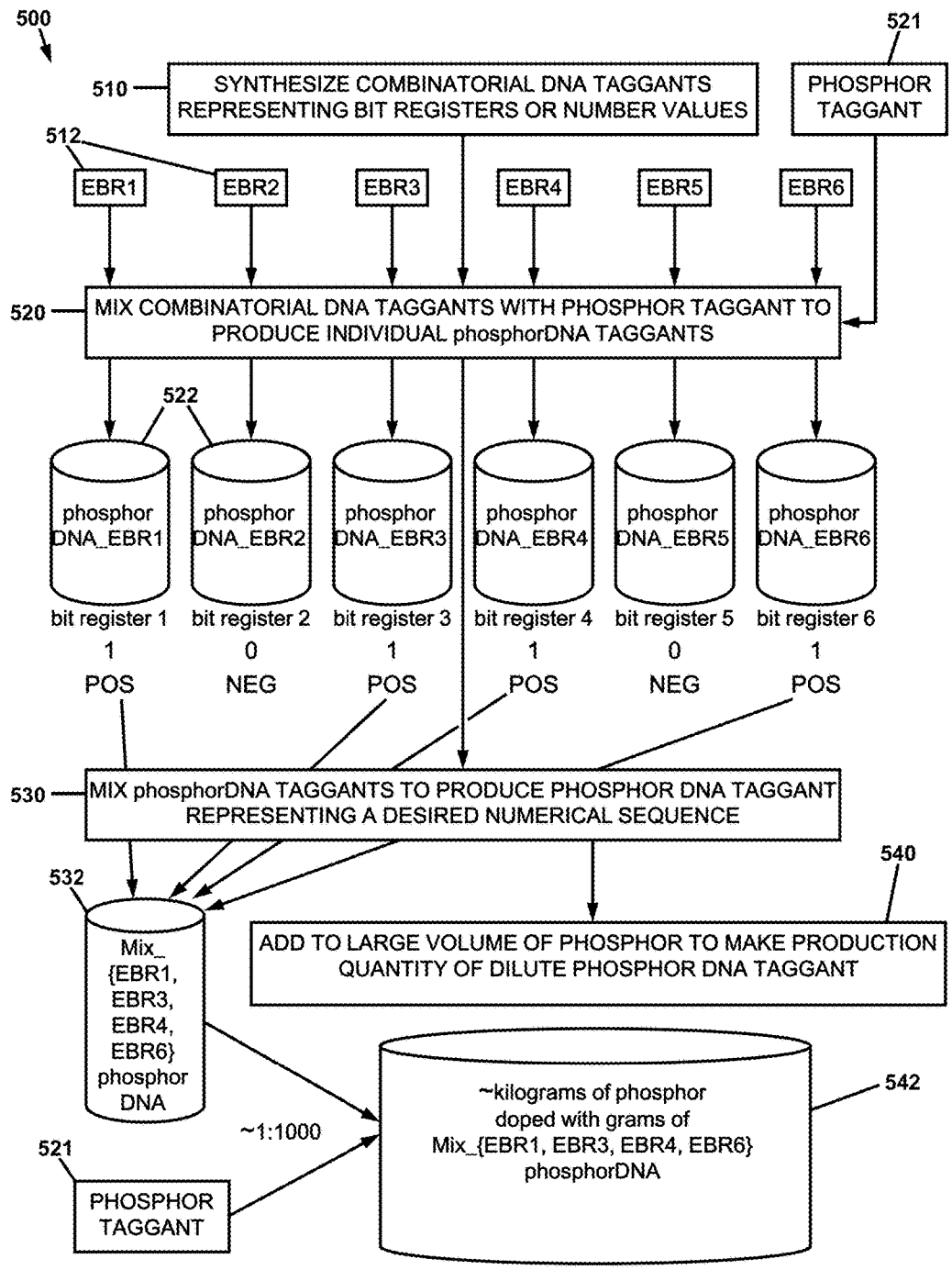
FIG. 14 is a flowchart depicting a method of preparing a layered taggant comprising a combinatorial DNA taggant and a non-DNA taggant.

This method is illustrated in FIG. 14 using the above numerical sequence and phosphorDNA_1010101 as an example. The method 500 comprises synthesizing 510 the desired combinatorial taggants 512 that represent number values or bit registers, such as taggants 512 prepared according to methods 100, 400, or 450 described previously herein. The combinatorial DNA taggants 512 are then mixed 520 with a non-DNA taggant. As shown in FIG. 14, the non-DNA taggant may be an upconverting phosphor. Other non-DNA taggants are contemplated. Mixing 520 the bit register/number value taggants 512 with a phosphor taggant 521 produces individual phosphor DNA taggants 522.

These individual phosphorDNA taggants 522 may be blended 530 to produce a Mix_phosphorDNA taggant 532, which may represent a numerical sequence, such as mixing to provide Mix_{EBR1, EBR3, EBR4, EBR6}phosphorDNA representing 101101 as recited in the above example and shown in FIG. 14. The Mix_phosphorDNA taggant 532 may be further diluted 542 with phosphor taggant 521 to produce manufacturing scale quantities of phosphorDNA taggant for use as a layered taggant. This layered taggant may have a DNA concentration on the order of tenths of a part per trillion, while still being detectable by the PCR methods recited herein.

The above method has been verified experimentally with the ComDTag (01234)(01211) of Table 5. In an experiment, 40 milliliters of 4 nanomolar aqueous ComDTag (01234) (00000) was added to 40 grams of the up-converting phosphor MicroTagg of BrandWatch Technologies. This was followed by drying, which produced 40 grams of phosphorDNA containing 0.1 nanomole per gram of the ComDTag (01234)(00000). This ComDTag was detected by the PCR method at that concentration, and also at a further aqueous dilution of $10^{-6}$. This latter concentration is on the order of 0.25 parts per trillion. Thus the instant combinatorial DNA taggants are known to be detectable at extremely low concentrations.

Taggant Design and Synthetic DNA Code (SynDCode) Software

The decoding accuracy of DNA taggants using the PCR method depends upon whether or not so-called false priming sites exist in the taggants. The priming sites for the Applicant's method may be one or more of the table-mers used to construct the taggants, depending upon how long the table-mers are. False priming site sequences can arise if two or more of the table-mers are too similar, or if the taggant sequence regions that overlap the junctions where table-mers are concatenated are too similar to the original table sequences.

To prevent this problem from occurring, the Applicant uses synthetic DNA code software, SynDCode, to design the set of table-mers in a given table. SynDCode is a software tool developed by the Applicant to design synthetic DNA sequences to be used in biologically based information systems. Details on the algorithms and use of SynDCode may be found in Air Force Research Laboratory's Final Technical Report AFRL-RI-RS-TR-2007-288, January 2008, "Superimposed Code Theoretic Analysis of DNA Codes and DNA Computing," by A. Macula, the disclosure of which is incorporated herein by reference. Examples of the use of SynDCode to generate DNA code sequences are disclosed in *Natural Computing*, Vol. 8, Issue 2, 2009, "Successful preparation and analysis of a 5-site 2-variable DNA library," of Gal et al. Additional descriptions of SynDCode methods and applications can also be found in the following references:

Arkadii G. D'yachkov, Anthony J. Macula, Wendy K. Pogozelski, Thomas E. Renz, Vyacheslav V. Rykov, David C. Torney: A Weighted Insertion-Deletion Stacked Pair Thermodynamic Metric for DNA Codes. DNA 2004: 90-103;

Arkadii G. D'yachkov, Anthony J. Macula, Wendy K. Pogozelski, Thomas E. Renz, Vyacheslav V. Rykov, David C. Torney: New t-Gap Insertion-Deletion-Like Metrics for DNA Hybridization Thermodynamic Modeling. *Journal of Computational Biology* 13(4): 866-881 (2006);

Morgan A. Bishop, Arkadii G. D' yachkov, Anthony J. Macula, Thomas E. Renz, Vyacheslav V. Rykov: Free Energy Gap and Statistical Thermodynamic Fidelity of DNA Codes. *Journal of Computational Biology* 14(8): 1088-1104 (2007); and Anthony J. Macula, Alexander Schliep, Morgan A. Bishop, Thomas E. Renz: New, Improved, and Practical k-Stem Sequence Similarity Measures for Probe Design. *Journal of Computational Biology* 15(5): 525-534 (2008).

To summarize, SynDCode enables the specification of thermodynamic distance and dissimilarity of the nucleotides in a DNA sequence such that the synthetic table-mers (and their complements) do not create false priming sites. The table-mers in the tables provided herein were designed by SynDCode to be non-complementary and non-cross-hybridizing so that each position in a taggant library strand is extremely highly specific for a unique PCR primer. It is known that SynDCode provides non-cross-hybridizing output via repeated experimental verification in the laboratory.

It is, therefore, apparent that there has been provided, in accordance with the present invention, combinatorial DNA taggants and methods of making and using such taggants. Having thus described the basic concepts of the invention, it will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed methods to any order except as may be specified in the claims.

I claim:

1. A method of making a combinatorial DNA taggant comprising:
   defining a set of n unique first single stranded DNA strands $S_1$ through $S_n$ and n unique reverse complement strands $CS_1$ through $CS_n$ of the first single stranded DNA strands, wherein n is a natural number having a value greater than 2; and
   synthesizing a set of n(n−1)/2 unique bit register single stranded encoding strands comprised of base sequences by:
      synthesizing n−1 of the n(n−1)/2 unique bit register single stranded encoding strands, the base sequences of which are synthesized by combining the base sequences of the first of the n unique single stranded DNA strands $S_1$ with the base sequences of each of reverse complement strand $CS_2$ through $CS_n$, wherein for each of the n−1 unique bit register single stranded encoding strands, there are no nucleotide bases between the 3' end of the respective unique single stranded DNA strand and the 5' end of the unique reverse complement strand; and
      synthesizing unique single stranded DNA strands, the base sequences of which are synthesized by combining the base sequences of each of the unique single stranded DNA strands $S_i$ through $S_{n-1}$, with the base sequences of each of the reverse complement strands $CS_{i+1}$ through $CS_n$, where i has an initial value of 2, thereby producing the unique bit register single stranded encoding strands, and wherein for each of the unique bit register single stranded encoding strands, there are no nucleotide bases between the 3' end of the respective unique single stranded DNA strand and the 5' end of the unique reverse complement strand.

2. The method of claim 1, further comprising selecting a subset of the n(n−1)/2 unique bit register encoding strands as the combinatorial DNA taggant.

3. The method of claim 2, wherein the selected subset of the n(n−1)/2 unique bit register encoding strands are mixed into a single liquid solution to make the combinatorial DNA taggant.

4. The method of claim 2, wherein the n(n−1)/2 unique bit register encoding strands are prepared in n(n−1)/2 separate liquid solutions, and the method further comprises mixing the liquid solutions of the selected subset of the n(n−1)/2 unique bit register encoding strands to make the combinatorial DNA taggant.

5. The method of claim 4, wherein the selected subset of the n(n−1)/2 unique bit register encoding strands are mixed into a single liquid solution to make the combinatorial DNA taggant.

* * * * *

SEQUENCE LISTING

<160> NUMBER OF SEQ ID NOS: 90

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgtccatcgt                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cattcgcgga                                                          10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acagttgccg                                                          10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcggtaagcg                                                          10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gagcgaacca                                                          10

<210> SEQ ID NO 6
<211> LENGTH: 10
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 6
gcagaagcca                                                                  10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cgcaagctga                                                                  10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agtggatgcg                                                                  10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgcacgagac                                                                  10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcggagtgct                                                                  10

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgtccatcgt cgcaagctga agtggatgcg tcggtaagcg tcggagtgct                      50

<210> SEQ ID NO 12
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 12
agcactccga                                                                10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgtccatcgt                                                                10

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgtccatcgt cattcgcgga acagttgccg tcggtaagcg gagcgaacca                     50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcagaagcca cattcgcgga acagttgccg tcggtaagcg gagcgaacca                     50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cgtccatcgt cgcaagctga acagttgccg tcggtaagcg gagcgaacca                     50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gcagaagcca cgcaagctga acagttgccg tcggtaagcg gagcgaacca                     50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 18
cgtccatcgt cattcgcgga agtggatgcg tcggtaagcg gagcgaacca         50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gcagaagcca cattcgcgga agtggatgcg tcggtaagcg gagcgaacca         50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cgtccatcgt cgcaagctga agtggatgcg tcggtaagcg gagcgaacca         50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gcagaagcca cgcaagctga agtggatgcg tcggtaagcg gagcgaacca         50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgtccatcgt cattcgcgga acagttgccg tgcacgagac gagcgaacca         50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcagaagcca cattcgcgga acagttgccg tgcacgagac gagcgaacca         50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 24
cgtccatcgt cgcaagctga acagttgccg tgcacgagac gagcgaacca          50

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcagaagcca cgcaagctga acagttgccg tgcacgagac gagcgaacca          50

<210> SEQ ID NO 26
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cgtccatcgt cattcgcgga agtggatgcg tgcacgagac gagcgaacca          50

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcagaagcca cattcgcgga agtggatgcg tgcacgagac gagcgaacca          50

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cgtccatcgt cgcaagctga agtggatgcg tgcacgagac gagcgaacca          50

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcagaagcca cgcaagctga agtggatgcg tgcacgagac gagcgaacca          50

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 30
cgtccatcgt cattcgcgga acagttgccg tcggtaagcg tcggagtgct              50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcagaagcca cattcgcgga acagttgccg tcggtaagcg tcggagtgct              50

<210> SEQ ID NO 32
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgtccatcgt cgcaagctga acagttgccg tcggtaagcg tcggagtgct              50

<210> SEQ ID NO 33
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcagaagcca cgcaagctga acagttgccg tcggtaagcg tcggagtgct              50

<210> SEQ ID NO 34
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cgtccatcgt cattcgcgga agtggatgcg tcggtaagcg tcggagtgct              50

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcagaagcca cattcgcgga agtggatgcg tcggtaagcg tcggagtgct              50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
```
gcagaagcca cgcaagctga agtggatgcg tcggtaagcg tcggagtgct        50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgtccatcgt cattcgcgga acagttgccg tgcacgagac tcggagtgct        50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcagaagcca cattcgcgga acagttgccg tgcacgagac tcggagtgct        50

<210> SEQ ID NO 39
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgtccatcgt cgcaagctga acagttgccg tgcacgagac tcggagtgct        50

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcagaagcca cgcaagctga acagttgccg tgcacgagac tcggagtgct        50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cgtccatcgt cattcgcgga agtggatgcg tgcacgagac tcggagtgct        50

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcagaagcca cattcgcgga agtggatgcg tgcacgagac tcggagtgct            50

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgtccatcgt cgcaagctga agtggatgcg tgcacgagac tcggagtgct            50

<210> SEQ ID NO 44
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gcagaagcca cgcaagctga agtggatgcg tgcacgagac tcggagtgct            50

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgtccatcgt cgcaagctga agtggatgcg                                  30

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgtccatcgt cgcaagctga tcggagtgct                                  30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
agtggatgcg tcggtaagcg tcggagtgct                                  30

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cgtccatcgt cgcaagctga tcggtaagcg                                  30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcaactctta cctcaatctc atacca                                          26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atcttctcct ccaatccatt tctcat                                          26

<210> SEQ ID NO 51
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctctcactct ctcactcctt atcaat                                          26

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttcctaccaa aaccaaaaac tccaat                                          26

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atcatccact atcctctaca acactt                                          26

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aacaaccatt ctccaacctt catatt                                          26

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
catccttctt tcacttacac tcacat                                           26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tttccaattc caacataatc cacaca                                           26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aaatccacct tttcacaaaa ctacct                                           26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caaaacaaac actcaactac actctc                                           26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tcaaatcact accatctttt ccacaa                                           26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
acacacacaa caacaccaaa aataaa                                           26

```
<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
actcacacca atatctactt tctcct                                          26

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
aacctcctaa tcacctccta ttacac                                          26

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ttcacctctc ttcctaaatt cctctt                                          26

<210> SEQ ID NO 64
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
tcaactctta cctcaatctc ataccacatc cttctttcac ttacactcac attttccaat     60
tccaacataa tccacacaaa cctcctaatc acctcctatt acaccaaaac aaacactcaa    120
ctacactctc                                                          130

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gcgtgatagt tacttaacga tc                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
```

```
atcaacattg ctatactcac tg                                              22
```

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 67

```
tgttctgtac gagctagatt at                                              22
```

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 68

```
cacatcattc aacaatctga ga                                              22
```

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 69

```
gatcgttaag taactatcac gc                                              22
```

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 70

```
cagtgagtat agcaatgttg at                                              22
```

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 71

```
ataatctagc tcgtacagaa ca                                              22
```

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 72

```
tctcagattg ttgaatgatg tg                                              22
```

<210> SEQ ID NO 73
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gcgtgatagt tacttaacga tccagtgagt atagcaatgt tgat        44

<210> SEQ ID NO 74
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gcgtgatagt tacttaacga tcataatcta gctcgtacag aaca        44

<210> SEQ ID NO 75
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcgtgatagt tacttaacga tctctcagat tgttgaatga tgtg        44

<210> SEQ ID NO 76
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
atcaacattg ctatactcac tgataatcta gctcgtacag aaca        44

<210> SEQ ID NO 77
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
atcaacattg ctatactcac tgtctcagat tgttgaatga tgtg        44

<210> SEQ ID NO 78
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
tgttctgtac gagctagatt attctcagat tgttgaatga tgtg        44

```
<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
aagagttgtc attactcgaa tg                                           22

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
cattcgagta atgacaactc tt                                           22

<210> SEQ ID NO 81
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gcgtgatagt tacttaacga tccattcgag taatgacaac tcttcagtga gtatagcaat  60
gttgat                                                             66

<210> SEQ ID NO 82
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gcgtgatagt tacttaacga tccattcgag taatgacaac tcttataatc tagctcgtac  60
agaaca                                                             66

<210> SEQ ID NO 83
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gcgtgatagt tacttaacga tccattcgag taatgacaac tctttctcag attgttgaat  60
gatgtg                                                             66

<210> SEQ ID NO 84
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 84
atcaacattg ctatactcac tgcattcgag taatgacaac tcttataatc tagctcgtac        60
agaaca                                                                   66

<210> SEQ ID NO 85
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
atcaacattg ctatactcac tgcattcgag taatgacaac tctttctcag attgttgaat        60
gatgtg                                                                   66

<210> SEQ ID NO 86
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tgttctgtac gagctagatt atcattcgag taatgacaac tctttctcag attgttgaat        60
gatgtg                                                                   66

<210> SEQ ID NO 87
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caaccaacca ctctaccaac cctacaccac ctacacctttt cctttcctcc atcacctcat        60
cctcactctc acttccttca tctcctctcc actcaaaacc                              100

<210> SEQ ID NO 88
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
ccaaacctcc actttccaac acacaactcc tccacaatca tcacacacac acacacaatt        60
cacctctctc acttcttcca tctcctctcc actcaaaacc                              100

<210> SEQ ID NO 89
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
caaccaacca ctctaccaac cctacaccac ctacaccttt tcacacacac acacacaatt        60
```

```
cctcactctc acttccttca tctcctctcc actcaaaacc                          100
```

<210> SEQ ID NO 90
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
caaccaacca ctctaccaac cctacaccac ctacaccttt tcacacacac acacacaatt    60
cacctctctc acttcttcca tctcctctcc actcaaaacc                          100
```